US012745899B2

(12) United States Patent
Corbeil et al.

(10) Patent No.: US 12,745,899 B2
(45) Date of Patent: Sep. 29, 2026

(54) # DEVICES, SYSTEMS, AND METHODS TO SUPPLY FLUIDS TO AN ENDOSCOPE

(71) Applicant: Boston Scientific Scimed, Inc., Maple Grove, MN (US)

(72) Inventors: Scott Edward Corbeil, Litchfield, NH (US); Ryan V. Wales, Northborough, MA (US); Ryan Evers, Billerica, MA (US); James J. Scutti, Norwell, MA (US); Christopher A. Benning, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 242 days.

(21) Appl. No.: 18/602,919

(22) Filed: Mar. 12, 2024

(65) Prior Publication Data

US 2024/0306902 A1 Sep. 19, 2024

Related U.S. Application Data

(60) Provisional application No. 63/489,865, filed on Mar. 13, 2023.

(51) Int. Cl.
*A61B 1/015* (2006.01)
*A61B 1/12* (2006.01)

(52) U.S. Cl.
CPC .............. *A61B 1/015* (2013.01); *A61B 1/126* (2013.01); *Y10T 137/4857* (2015.04); *Y10T 137/85978* (2015.04); *Y10T 137/86027* (2015.04)

(58) Field of Classification Search
CPC ..... Y10T 137/86027; Y10T 137/87249; Y10T 137/86043; Y10T 137/86276;
(Continued)

(56) References Cited

U.S. PATENT DOCUMENTS 4,261,343 A * 4/1981 Ouchi ...................... A61B 1/12 600/158
4,325,362 A * 4/1982 Ouchi ...................... A61B 1/12 600/158
(Continued)

FOREIGN PATENT DOCUMENTS

JP 2000225186 A 8/2000

OTHER PUBLICATIONS

Invitation To Pay Additional Fees and, Where Applicable, Protest Fee for International Application No. PCT/US2024/019564, dated Jul. 1, 2024. (13 pages).

*Primary Examiner* — Matthew W Jellett
(74) *Attorney, Agent, or Firm* — Seager, Tufte & Wickhem, LLP

(57) ABSTRACT

Methods and systems for providing a flow of fluid to an endoscope. An illustrative container, manifold, and tubing set arranged and configured to couple to an endoscope may comprise a fluid container, a manifold fluidly coupled to the fluid container, and one or more tubing sets coupled to the manifold. The manifold may include an irrigation conduit for providing irrigation fluid from the fluid container to the endoscope, a lens wash chamber configured to receive liquid from the irrigation conduit. In some cases, the manifold may include a pressurized chamber and an adjustable barrier or divider between the pressurized chamber and the lens wash chamber. The adjustable barrier or divider may adjust to push liquid through an outlet in communication with the lens wash chamber in response to the pressurized chamber receiving pressurized gas.

17 Claims, 14 Drawing Sheets

(58) Field of Classification Search

CPC ..... Y10T 137/86083; Y10T 137/86051; Y10T 137/7781; Y10T 137/7783; Y10T 137/7787; Y10T 137/4857; Y10T 137/4841; Y10T 137/789; Y10T 137/7897; Y10T 137/7888; Y10T 137/7885; Y10T 137/784; Y10T 137/7887; Y10T 137/7886; Y10T 137/7884; Y10T 137/87885; Y10T 137/87829; A61B 1/015; A61B 1/126; A61B 1/00068; A61B 1/00128; A61B 1/00119; A61B 1/00133; F16K 15/148; F16K 15/1402; F16K 15/144; F16K 15/147; F16K 15/16; F16K 15/1471; F16K 15/145; F16K 15/1472; F16K 15/14

USPC .................................................. 600/156, 158

See application file for complete search history.

(56) References Cited

U.S. PATENT DOCUMENTS 4,548,197 A * 10/1985 Kinoshita ................ A61B 1/12 604/93.01
4,552,130 A * 11/1985 Kinoshita .......... A61B 1/00068 604/93.01
4,562,830 A * 1/1986 Yabe ........................ A61B 1/12 604/119
4,760,838 A * 8/1988 Fukuda .................. A61B 1/126 600/158
4,844,052 A * 7/1989 Iwakoshi ............... A61B 1/126 600/157
5,133,336 A 7/1992 Savitt et al.
5,515,851 A * 5/1996 Goldstein ........... A61M 3/0233 600/431
6,558,317 B2 * 5/2003 Takahashi .............. A61B 1/015 600/158
7,591,783 B2 * 9/2009 Boulais ................ A61B 1/0008 600/141
8,083,671 B2 * 12/2011 Boulais .............. A61B 1/00068 600/156
8,118,732 B2 * 2/2012 Banik ...................... A61B 1/05 600/152
8,535,219 B2 * 9/2013 Smith .................. A61B 1/0676 600/179
8,870,756 B2 10/2014 Maurice
9,167,958 B2 * 10/2015 Banik ...................... A61B 1/31
9,649,437 B2 * 5/2017 Eubanks ........ A61B 17/320758
11,076,840 B2 * 8/2021 Furlong ........... A61B 17/32002
2003/0032862 A1 * 2/2003 Ota ........................ A61B 1/015 600/158
2006/0276689 A1 * 12/2006 Litscher ................. A61B 1/015 600/156
2010/0256448 A1 * 10/2010 Smith .................. A61B 1/0008 600/156
2012/0302836 A1 11/2012 Boulais et al.
2017/0368240 A1 12/2017 Cheng
2022/0192478 A1 6/2022 Pollock et al.
2022/0192479 A1 6/2022 Harris et al.

* cited by examiner

DEVICES, SYSTEMS, AND METHODS TO SUPPLY FLUIDS TO AN ENDOSCOPE

CROSS-REFERENCE TO RELATED APPLICATIONS

This application claims the benefit of U.S. Provisional Patent Application Ser. No. 63/489,865 filed on Mar. 13, 2023, the disclosure of which is incorporated herein by reference.

FIELD

This disclosure relates generally to medical devices and methods, and particularly to a container, manifold, and tubing sets to supply fluid and/or gas to an endoscope.

BACKGROUND

A wide variety of intracorporeal and extracorporeal medical devices and systems have been developed for medical use, for example, for endoscopic procedures. Some of these devices and systems include guidewires, catheters, catheter systems, endoscopic instruments, and the like. These devices and systems are manufactured by any one of a variety of different manufacturing methods and may be used according to any one of a variety of methods. Of the known medical devices, systems, and methods, each has certain advantages and disadvantages. There is an ongoing need to provide alternative medical devices and systems as well as alternative methods for manufacturing and using medical devices and systems.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, a manifold for use with an endoscope system may include a fluid inlet, a first fluid outlet, a second fluid outlet, a conduit in fluid communication with the fluid inlet and the first fluid outlet, a pressurized chamber, a compressible chamber in fluid communication with the conduit and in communication with the pressurized chamber, and wherein a volume of the compressible chamber is configured to be reduced to cause fluid to pass through the second fluid outlet in response to a pressurized gas received at the pressurized chamber.

Alternatively or additionally to any of the examples above, the manifold may further include a one-way valve between the conduit and the compressible chamber, wherein the one-way valve may be configured to allow fluid to pass from the conduit into the compressible chamber and prevent fluid from passing to the conduit from the compressible chamber.

Alternatively or additionally to any of the examples above, the pressurized chamber may be configured to receive pressurized air from an air pump.

Alternatively or additionally to any of the examples above, the pressurized chamber may be configured to receive pressurized carbon dioxide ($CO_2$).

Alternatively or additionally to any of the examples above, the manifold may further include a gas port configured to receive the pressurized gas.

Alternatively or additionally to any of the examples above, the manifold may further include an adjustable barrier between the compressible chamber and the pressurized chamber.

Alternatively or additionally to any of the examples above, the adjustable barrier may adjust to decrease the volume of the compressible chamber and increase a volume of the pressurized chamber in response to the pressurized chamber receiving the pressurized gas.

Alternatively or additionally to any of the examples above, the adjustable barrier may comprise a plunger configured to form a seal with a wall defining the compressible chamber and the pressurized chamber.

Alternatively or additionally to any of the examples above, the manifold may further include a spring in communication with the plunger, wherein the spring may be configured to bias the plunger to a first position associated with a first volume of the compressible chamber and the plunger is configured to adjust to a second position associated with a second volume of the compressible chamber in response to a pressure in the pressurized chamber acting on the plunger to overcome the bias of the spring.

Alternatively or additionally to any of the examples above, the adjustable barrier may comprise a flexible membrane between the compressible chamber and the pressurized chamber.

Alternatively or additionally to any of the examples above, the flexible membrane may be biased to a first position associated with a first volume of the compressible chamber and the flexible membrane may be configured to adjust to a second position associated with a second volume of the compressible chamber in response to a pressure in the pressurized chamber acting on the flexible membrane to overcome the bias.

Alternatively or additionally to any of the examples above, the manifold may further include a gas port in communication with the pressurized chamber and configured to receive the pressurized gas, wherein the gas port and the second fluid outlet are configured to couple with a coaxial dual lumen tubing set.

Alternatively or additionally to any of the examples above, the manifold may further include a fluid access port in fluid communication with the conduit between the fluid inlet and the first fluid outlet.

In another example, a fluid supply system for an endoscope system may include a container configured to contain fluid, and a manifold including a pressurized gas pathway, a first fluid pathway configured to receive fluid from the container, a second fluid pathway configured to receive fluid from the container, a first port in fluid communication with the pressurized gas pathway, a second port in fluid communication with the first fluid pathway, and a third port in fluid communication with the second fluid pathway. The fluid supply system may further include a first tubing set having a first end configured to couple to the second port and to be in communication with a pump and a second tubing set having a first end configured to couple to the third port and to be in fluid communication with an endoscope of the endoscope system.

Alternatively or additionally to any of the examples above, the first tubing set may be releasably coupled to the second tubing set.

Alternatively or additionally to any of the examples above, the first tubing set may include a pump engaging portion at a location between the first end a second end of the first tubing set.

Alternatively or additionally to any of the examples above, the manifold may further include a first bag spike configured to engage the container and in fluid communication with the pressurized gas pathway to provide pressurized gas to the container, and a second bag spike configured to engage the container and in fluid communication with the first fluid pathway and the second fluid pathway.

Alternatively or additionally to any of the examples above, the manifold comprises a recess configured to receive the container and the first bag spike and the second bag spike extend from a surface of the recess.

Alternatively or additionally to any of the examples above, the manifold may include a pressurized chamber configured to expand in response to receiving pressurized fluid via the pressurized gas pathway and cause fluid to be output from the third port.

In another example, a manifold for use with an endoscope system may include an irrigation conduit configured to be in fluid communication with a source of fluid, a lens wash chamber configured to receive liquid from the irrigation conduit via an inlet and output the liquid received from an outlet, a pressurized chamber configured to receive pressurized gas, and an adjustable barrier between the pressurized chamber and the lens wash chamber, wherein the adjustable barrier may be configured to adjust to push liquid through the outlet in response to the pressurized chamber receiving the pressurized gas.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
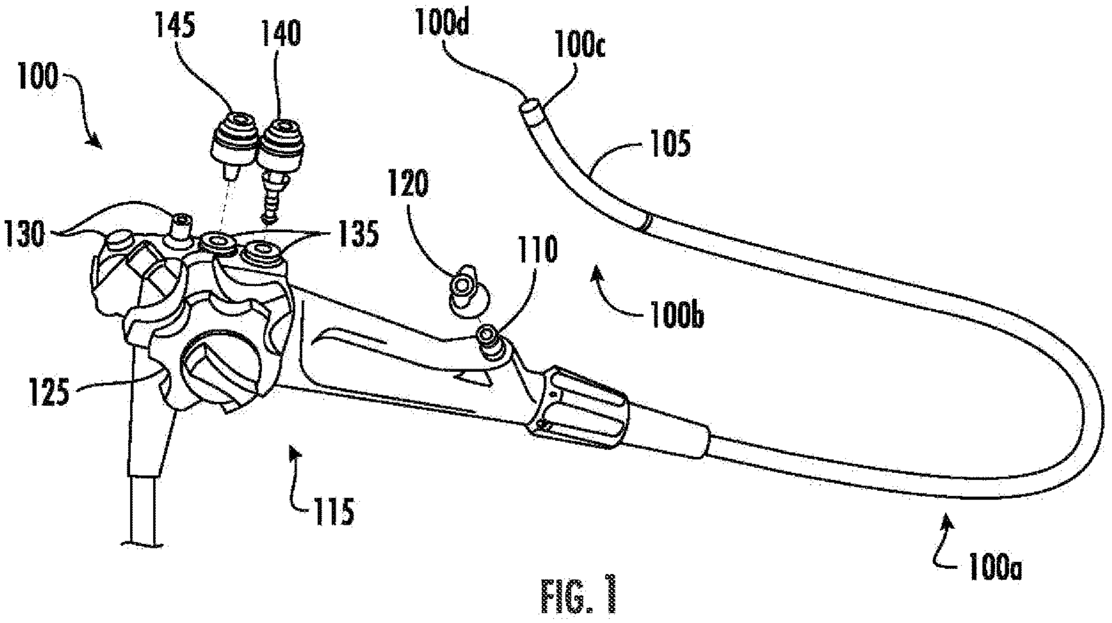
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an illustrative medical system that may be used in endoscopic medical procedures. However, it should be noted that reference to this particular procedure is provided only for convenience and not intended to limit the disclosure. The concepts underlying the disclosed devices, systems, assemblies, and/or related methods of use may be utilized in any suitable procedure, medical or otherwise. This disclosure may be understood with reference to the following description and the appended drawings, wherein like elements are referred to with the same reference numerals.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features, and/or specifications are disclosed, one of skill in the art, incited by the present disclosure, would understand desired dimensions, ranges, and/or values may deviate from those expressly disclosed.

As used in this specification and the appended claims, the singular forms “a”, “an”, and “the” include plural referents unless the content clearly dictates otherwise. As used in this specification and the appended claims, the term “or” is generally employed in its sense including “and/or” unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

It is noted that references in the specification to “an embodiment”, “some embodiments”, “other embodiments”, etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is illustrative only. In some embodiments, alterations of and deviations from previously-used numerical nomenclature may be made in the interest of brevity and clarity. That is, a feature identified as a “first” element may later be referred to as a “second” element, a “third” element, etc. or may be omitted entirely, and/or a different feature may be referred to as the “first” element. The meaning and/or designation in each instance will be apparent to the skilled practitioner.

The detailed description is intended to illustrate but not limit the disclosure. The various elements described may be arranged in various combinations and configurations without departing from the scope of the disclosure. The detailed description illustrates example embodiments of the disclosure.

An endoscope is used in performing diagnostic and/or therapeutic treatments by inserting an elongated shaft of the endoscope into a subject to observe a part to be examined within a body cavity of the subject and, if necessary, inserting a treatment instrument/tool into a working channel in the elongated shaft of the endoscope. During endoscopic procedures, having a clear field of vision is important to provide accurate diagnosis and therapies to patients. During these procedures, blood, tissue, fecal matter, mucus, etc. can foul up the lens, resulting in visual impairment. As a result, physicians spend time during the procedure cleaning the endoscope lens and lumen.

Endoscopes or endoscope systems may include a fluid/lens wash capability, or the like, configured to feed fluid, such as gas (e.g., air, $CO_2$), to an end of the endoscope for insufflating the inside of the subject at a target site. Lens wash features may provide sterilized water at relatively high pressure to spray across and clear debris from a camera lens of the endoscope. In order to rinse the target site of the subject, separate from the air/water feed capability, endoscopes or endoscope systems may have an irrigation capability that provides lower pressure, higher volume water, supplied via a pump (e.g., a peristaltic pump) to the target site in order to clear the field of view for observation and treatment. A fluid supply system for an endoscope may have a water source (e.g., a fluid source) for lens wash and/or irrigation features that may include one or more fluid reservoirs having tubing and fitting (e.g., caps, covers, ports, etc.) assemblies that create a plumbing circuit in connection with the endoscope channels, valving, and/or connectors to accomplish the gas and water functions described.

Tubing and fitting assemblies may be available in various configurations, which may include or be configured to be in communication with a reservoir or other suitable fluid source (e.g., one or more water bottles, bags, etc.), a fitting fitted for the specific fluid source, and an array of tubing (e.g., one or more tubing sets) that is extendable through openings and/or configured to connect to connectors or ports in the fitting or other portions of the fluid source. The tubing may be arranged to accommodate a specific configuration of endoscope fittings and valving, which does not tend to be modular or optional. In some cases, one or more connectors or ports may be utilized to connect tubing for irrigation, lens wash, and/or insufflation features to an endoscope umbilical in fluid communication with working channels of the endoscope.

Figure 2:
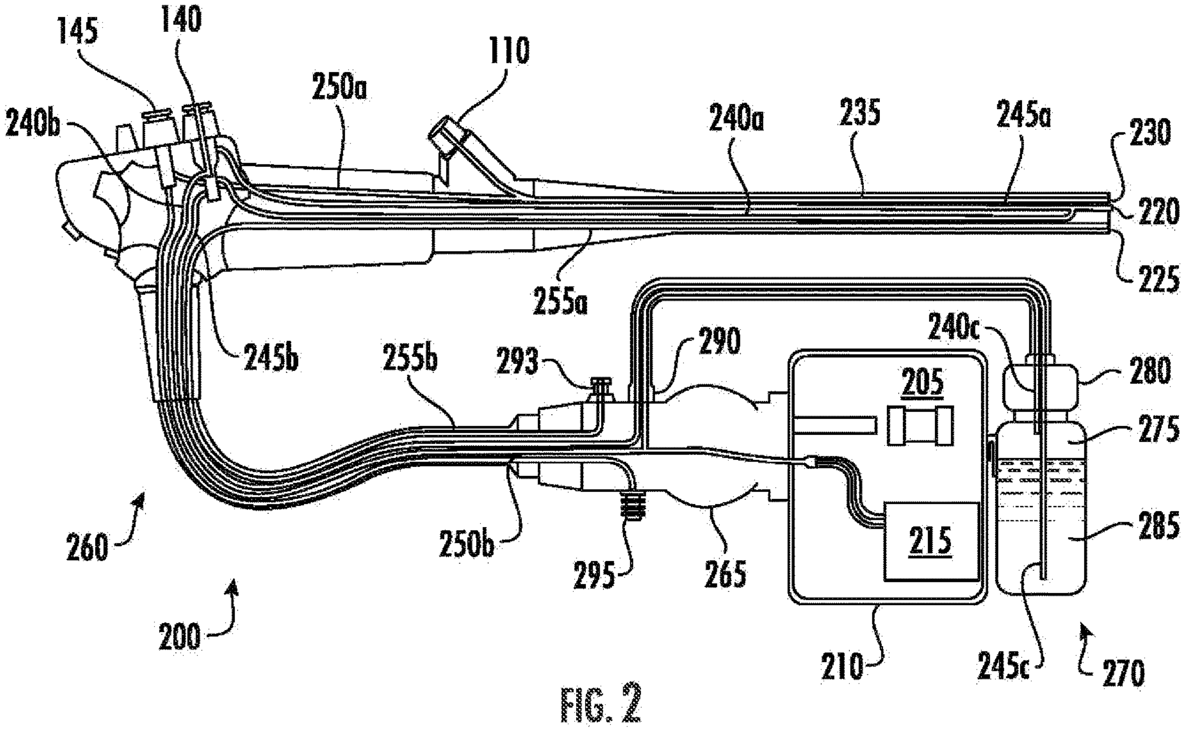
FIG. 2 depicts components of an endoscope system with endoscope, light source, light source connector, water reservoir, and tubing assembly for air and lens wash fluid delivery.

With reference to FIG. 1, an illustrative endoscope 100 is depicted and FIG. 2 depicts an illustrative endoscope system 200. The endoscope 100 may include an elongated tube or shaft **100*a* that is configured to be inserted into a subject (e.g., a patient). Details of the endoscope 100 and the endoscope system 200** may be more fully described in U.S. Patent Application Publication No. 2022/0192479 A1, filed on Dec. 21, 2021, and titled TUBING ASSEMBLIES AND METHODS FOR FLUID DELIVERY, which is hereby incorporated by reference in its entirety for all purposes.

A light source 205 of the endoscope system 200 may feed illumination light to a distal portion **100*b* of the endoscope 100. The distal portion 100*b* of the endoscope 100 may house an imager (e.g., CCD or CMOS imager) (not shown). The light source 205 (e.g., a lamp) may be located in a video processing unit 210 that processes signals input from the imager and outputs processed video signals to a video monitor (not shown) for viewing. The video processing unit 210 may also serve as a component of an air/water feed circuit by housing a pressurizing or air pump 215, such as an air feed pump, in the unit 210**. Other suitable pumps for the air/water feed circuit are contemplated.

The endoscope shaft 100*a* may include a distal tip 100*c* (e.g., a distal tip unit) provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the subject at the treatment area and for supplying water to wash a lens covering the imager. An irrigation opening 225 in the end face 100*d* supplies irrigation fluid to the treatment area of the subject. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 may extend along the shaft 100*a* to a proximal channel opening 110 positioned distal to an operating handle 115 (e.g., a proximal handle) of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the flexible bending portion 105 (e.g., one knob may control up-down steering and another knob may control left-right steering). A plurality of video switches 130 for remotely operating the video processing unit 210 may be arranged on a proximal end side of the operating handle 115.

The operating handle 115 may be provided with dual valve locations 135. One of the valve locations 135 (e.g., locations at valve wells) may receive a gas/water valve 140 for operating an insufflating gas and lens water feed operation. A gas supply line 240*a* and a lens wash line 245*a* run distally from the gas/water valve 140 along the shaft 100*a* and converge at the distal tip 100*c* proximal to the gas/wash nozzle 220 (FIG. 2).

The other valve location 135 may receive a suction valve 145 for operating a suction operation. A suction supply line 250*a* may run distally from the suction valve 145 along the shaft 100*a* to a junction point in fluid communication with the working channel 235 of the endoscope 100.

The operating handle 115 may be electrically and fluidly connected to the video processing unit 210, via a flexible umbilical 260 and connector portion 265 extending therebetween. The flexible umbilical 260 may have a gas (e.g., air or $CO_2$) feed line 240*b*, a lens wash feed line 245*b*, a suction feed line 250*b*, an irrigation feed line 255*b*, a light guide (not shown), an electrical signal cable (not shown), and/or other suitable lines, guides, and/or cables. The connector portion 265 when plugged into the video processing unit 210 connects the light source 205 in the video processing unit with the light guide. The light guide may run along the umbilical 260 and the length of the endoscope shaft 100*a* to transmit light to the distal tip 100*c* of the endoscope 100. The connector portion 265, when plugged into the video processing unit 210, may also connect the air pump 215 to the gas feed line 240*b* in the umbilical 260.

A fluid source, such as a fluid or water container or reservoir 270 (e.g., water bottle, bag, etc.), a building water source, and/or other suitable fluid source, may be fluidly connected to the endoscope 100 through the connector portion 265 and the umbilical 260. A length of gas supply tubing 240*c* may pass from one end positioned in an air gap or gas 275 between the top 280 (e.g., a bottle cap, lid, closure, cover, etc.) of the reservoir 270 and the remaining water 285 (e.g., the remaining water 285) in the reservoir 270 to a connector 290 on the outside of the connector portion 265. The gas feed line 240*b* from the umbilical 260 branches in the connector portion 265 to fluidly communicate with the gas supply tubing 240*c* at the detachable connector 290, as well as the air pump 215. A length of lens wash tubing 245*c*, with one end positioned at the bottom of the reservoir 270, may pass through the top 280 of the reservoir 270 to the same detachable connector 290 as the gas supply tubing 240*c* on the connector portion 265. In other embodiments, the connections may be separate and/or separated from each other. The connector portion 265 may also have a detachable irrigation connection 293 for irrigation supply tubing (not shown) running from a source of irrigation water (not shown) to the irrigation feed line 255*b* in the umbilical 260. In some configurations, irrigation water may be supplied via a pump (e.g., a peristaltic pump) from a water source (not shown) independent from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100.

The gas feed line 240*b* and lens wash feed line 245*b* may be fluidly connected to the valve location 135 for the gas/water valve 140 and configured such that operation of the gas/water valve 140 in the well controls supply of gas or lens wash to the distal tip 100*c* of the endoscope 100. The suction feed line 250*b* is fluidly connected to the valve location 135 for the suction valve 145 and configured such that operation of the suction valve 145 in the well controls suction applied to the working channel 235 of the endoscope 100.

The gas supply tubing 240*c* and the lens wash tubing 245*c* may be combined in a coaxial relationship, but this is not required. In one example, the gas supply tubing 240*c* may define a lumen that is sufficiently large in diameter to encompass a smaller diameter lens wash tubing 245*c*, coaxially received within the gas supply tubing, as well as provide air to the water source in an annular space surrounding the lens wash tubing to pressurize the water reservoir. The lens wash tubing 245*c* may be configured to exit the lumen defined by the coaxial gas supply tubing in any suitable sealed manner, such as for example via an aperture, fitting, collar, and/or the link for the purpose of transitioning from the coaxial arrangement to a side-by-side arrangement of the detachable gas/lens wash connection to the endoscope connector portion 265.

FIGS. 3A-3D are schematic views illustrating operations of an embodiment of an endoscope system 300 (e.g., a medical device assembly), which may be similar or dissimilar to the endoscope system 200, where the supply tubing for irrigation and lens wash are connected to and drawn from a single water reservoir 270, 305 and/or other suitable fluid source. The hybrid system 300 may include the one or more water reservoir 270, 305 (e.g., a single water reservoir 305, as depicted in FIGS. 3A-3D), a cover or cap 310 (e.g., a fitting) to cover an opening of the reservoir 270, 305, gas supply tubing 240*c*, lens wash tubing 245*c*, irrigation pump 315 that may be in communication with foot switch 318 or other suitable switch, upstream irrigation tubing 255*c*, 320, and downstream irrigation supply tubing 255*c*.

The cap 310 may be configured to attach in a seal-tight manner (e.g., a hermetic seal or other suitable seal) to the water reservoir 270, 305 by a threaded arrangement and/or other suitable coupling mechanism. The cap 310 may include a gasket to seal the cap 310 to the reservoir 270, 305. The gasket may be an O-ring, flange, collar, and/or the like and can be formed of any suitable material. A number of through-openings (325*a*, 325*b*, 325*c*) in the cap 310 may be provided to receive, respectively, a length of gas supply tubing 240*c*, a length of lens wash tubing 245*c*, and a length of upstream irrigation supply tubing 320, but this is not required. Alternatively or additionally, the through-openings may be positioned at other locations on the reservoir, optionally independent of the cap 310. In FIGS. 3A-3D, the system depicted includes separate tubing for gas supply, lens wash, and irrigation.

In other embodiments, the gas supply tubing 240*c* and lens wash tubing 245*c* may be combined in a coaxial arrangement. For example, the gas supply tubing 240*c* may define a lumen that is sufficiently large in diameter to encompass a smaller diameter lens wash tubing, coaxially received within the gas supply tubing, as well as provide air to the water source in an annular space surrounding the lens wash tubing to pressurize the water reservoir. The lens wash tubing 245*c* may be configured to exit the lumen defined by the coaxial gas supply tubing in any suitable sealed manner, such as, for example, an aperture, fitting, collar, and/or the like, for the purpose of transitioning from the coaxial arrangement to a side-by-side arrangement at the detachable gas/lens wash connection to the endoscope connector portion 265 (e.g., FIG. 2).

In various embodiments, different configurations of valving may be incorporated into the tubing of the system 200, 300. For example, an in-flow check valve may be disposed in the path of the gas supply tubing 240*c* to help prevent liquid backflow into the air pump 215. In this manner, pressure building within the water reservoir 270, 305 may create a pressure difference between the water reservoir 270, 305 and the gas supply tubing 240*c* helping to maintain a positive pressure in the water reservoir 270, 305 even when large amounts of water may be removed from the water source during the irrigation function. This arrangement may compensate for any time lag in air being delivered from the air pump 215 to the water reservoir 270, 305, which might otherwise cause a negative pressure vacuum in the water reservoir 270, 305. Similarly, an out-flow check valve, such as a one-way valve, may be incorporated in the lens wash tubing 245*c*, upstream irrigation supply tubing 320, and/or downstream irrigation supply tubing 255*c* to help prevent backflow of water from either or both of the lens wash and irrigation tubing in the event of a negative pressure situation, as described.

More generally, in some configurations, a check valve may refer to any type of configuration for fluid to flow only in one direction in a passive manner. For example, a check valve may include, or refer to, one or more of a ball check valve, a diaphragm check valve, a swing check valve, a tilting disc check valve, a flapper valve, a stop-check valve, a lift-check valve, an in-line check valve, a duckbill valve, a pneumatic non-return valve, a reed valve, a flow check, a flapper valve, an umbrella valve, and/or other suitable check valve. Accordingly, a check valve as used herein may be meant to be separate and distinct from an active valve that is operated in a binary manner as an on/off valve or switch to allow flow to be turned on or allow flow to be turned off (e.g., a stop cock valve, solenoid valve, peristaltic pump, blow off valve).

During operation of the system of FIGS. 3A-3D, a flow of water for irrigation may be achieved by operating the irrigation pump 315 via the foot switch 318 and/or other suitable actuation mechanism. A flow of water for lens wash may be achieved by depressing the gas/water valve 140 on the operating handle 115 of the endoscope 100. These functions may be performed independent of one another or simultaneously. When operating lens wash and irrigation at the same time, as fluid is removed from the water reservoir 270, 305, the pressure in the system may be controlled to maintain the lens wash tubing 245*c* at substantially the pressure necessary to accomplish a lower flow rate lens wash, while compensating for reduced pressure in the water reservoir 270, 305 due to supplying a high flow rate irrigation. When pressure is reduced in the water reservoir 270, 305 by use of the lens wash function, the irrigation function, or both functions simultaneously, the reduced pressure may be compensated for by the air pump 215 via the gas supply tubing 240*c*.

Flow paths in the schematic set-ups depicted in each of FIGS. 3A-3D have been highlighted to show the different flow paths possible with the hybrid system 300 having supply tubing (e.g., irrigation tubing 255*c*, 320, lens wash tubing 245*c*, and/or other suitable tubing) connected to and drawn from the single water reservoir 270, 305. Not all features depicted in each of FIGS. 3A-3D are labeled with reference numerals in each of FIGS. 3A-3D for clarity purposes, but similarly depicted features in FIGS. 3A-3D should be understood to be referring to a same or similar feature in each of FIGS. 3A-3D.

Figure 3A:
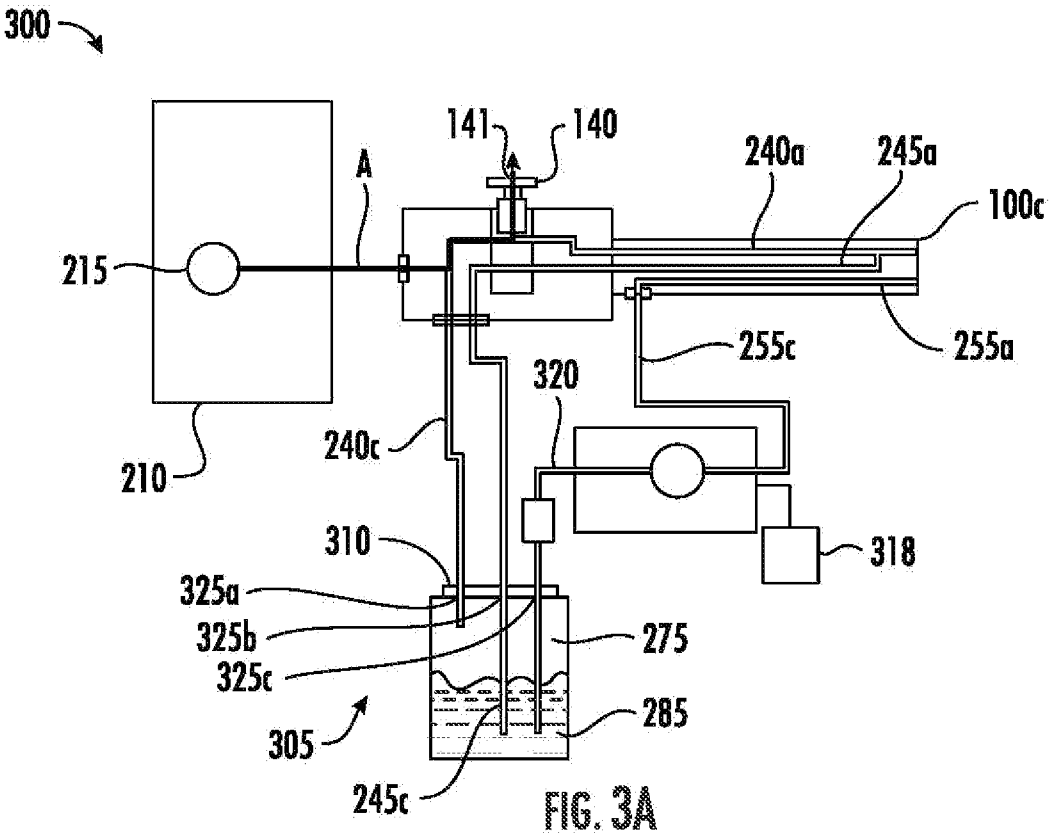
FIG. 3A depicts an endoscope system with endoscope, light source, water reservoir, and tubing assembly for hybrid air, lens wash and irrigation fluid delivery, wherein the system is activated to deliver air to atmosphere.

As shown in FIG. 3A, the endoscope 100 may be in a neutral state with the gas/water valve 140 in an open position. The neutral state delivers neither gas, nor lens wash fluid, to the distal tip of the endoscope. Rather gas (pressure) is delivered along path A from the pressurizing air pump 215 and vented through the gas feed line 240*b* (e.g., in the umbilical 260 via the connector portion 265, as depicted in FIG. 2) and through the gas/water valve 140 to atmosphere. Because the system is open at the vent hole in the gas/water valve 140, there is no build up to pressurize the water reservoir 270, 305 and consequently no water is pushed through the lens wash tubing 245*c*.

Figure 3B:
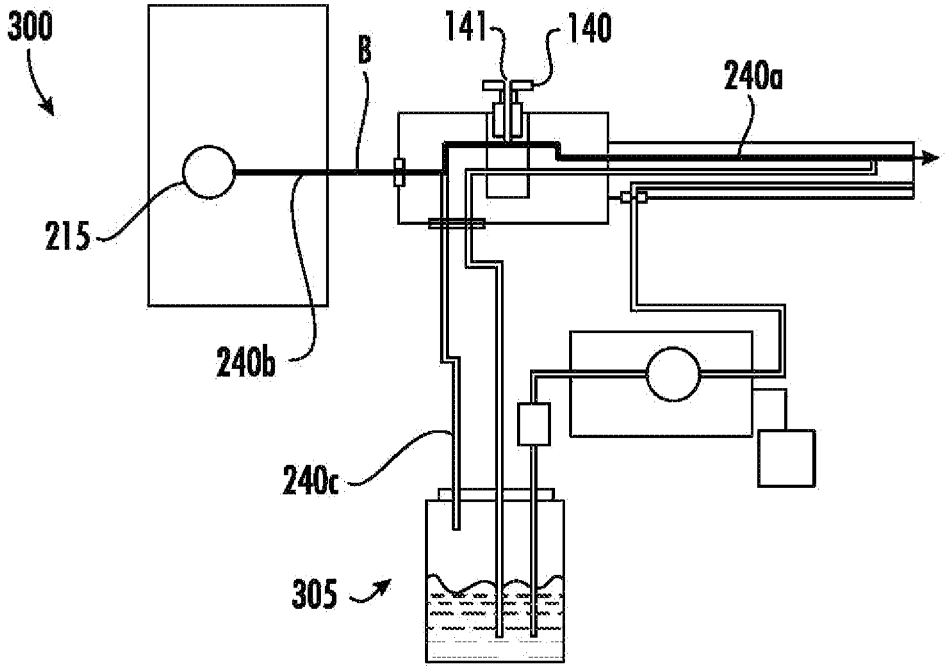
FIG. 3B depicts the endoscope system of FIG. 3A, wherein the system is activated to deliver air to a patient through the patient end of the endoscope.

As shown in FIG. 3B, the endoscope 100 may be in a gas delivery state with the gas/water valve 140 in a first position. When gas is called for at the distal tip 100*c*, for example, to clean the end face 100*d* of the distal tip 100*c* or insufflate the patient body in the treatment area, the user may close off a vent hole 141 in the gas/water valve 140 with a thumb, finger, or the like (first position). In this state, gas (pressure) may be delivered along path B from the air pump 215 and flowed through the gas feed line 240*b* (e.g., in the umbilical 260 via the connector portion 265, as depicted in FIG. 2). The gas may continue through the gas/water valve 140 to the gas supply line 240*a* in the endoscope shaft 100*a* and out the gas/lens wash nozzle 220 at the distal tip 100*c*. There is no build up to pressurize the water reservoir since the system is open at the gas/lens wash nozzle 220, and consequently no liquid is pushed through the lens wash tubing 245*c*.

Figure 3C:
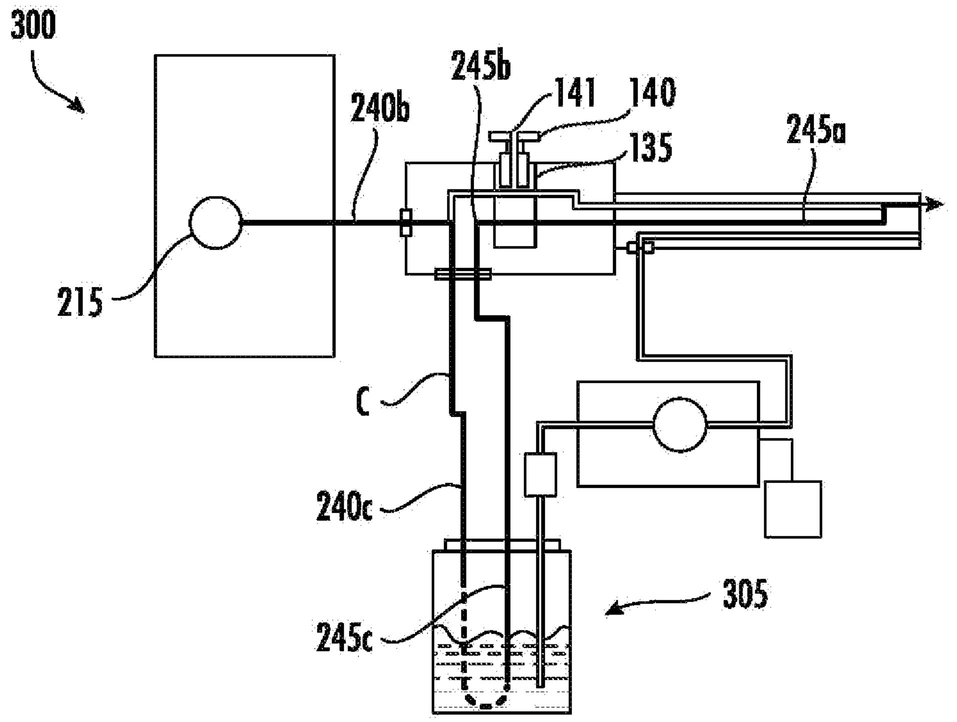
FIG. 3C depicts the endoscope system of FIG. 3A, wherein the system is activated to deliver lens wash fluid through the patient end of the endoscope.

As shown in FIG. 3C, the endoscope 100 may be in a lens wash delivery state with the gas/water valve 140 in a second position. When lens wash is called for at the distal tip 100*c*, for example, to clean the end face 100*d* of the distal tip 100*c*, the user, keeping the vent hole 141 in the gas/water valve 140 closed off, depresses the valve 140 to its furthest point in the valve location 135. The second position blocks off the gas supply to both atmosphere and the gas supply line 240*a* in the endoscope 100, and opens up the gas/water valve 140 to allow lens wash water to pass through to the lens wash line 245*a* in the endoscope shaft 100*a* and out the gas/lens wash nozzle 220 at the distal tip 100*c*. In this state, gas (pressure) is delivered along path C from the air pump 215, through the branched line in the connector portion 265 and out of the gas supply tubing 240*c* to the water reservoir 270, 305. The gas (pressure) pressurizes the surface of the remaining water 285 in the reservoir 270, 305 and pushes water up the lens wash tubing 245*c* (e.g., to the connector portion 265 of the umbilical 26, as depicted in FIG. 2. The pressurized lens wash water may be pushed further through the lens wash feed line 245*b* and through the gas/water valve 140. Because the system 300 is closed, gas pressure may be allowed to build and maintain a calibrated pressure level in the water reservoir 270, 305, rather than venting to atmosphere or being delivered to the patient. This pressure, along with the endoscope feed and supply lines and external tubing, translates to a certain range of flow rate of the lens wash.

Figure 3D:
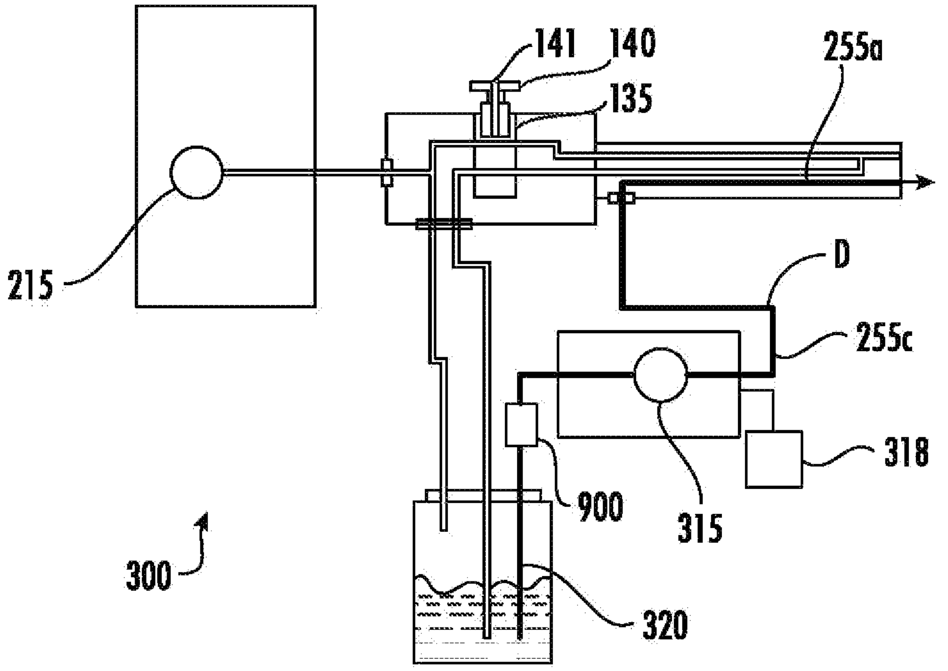
FIG. 3D depicts the endoscope system of FIG. 3A, wherein the system is activated to deliver irrigation fluid through the patient end of the endoscope.

As shown in FIG. 3D, the endoscope 100 is in an irrigation delivery state. This may be performed at the same or a different time from the delivery of gas and/or lens wash. When irrigation is called for at the distal tip 100*c*, for example, if visibility in the treatment area is poor or blocked by debris, or the like, the user may activate the irrigation pump 315 (e.g., by depressing foot switch 318 or other suitable actuation mechanism) to deliver water or other liquid from the reservoir 270, 305 along path D. With the pump 315 activated, water is sucked out of the water reservoir 270, 305 through the upstream irrigation supply tubing 255*c*, 320 and pumped along the downstream irrigation supply tubing 255*c* to the connector portion 265. The irrigation pump head pressure pushes the irrigation water further through the irrigation feed line 255*b* (e.g., extending through the umbilical 260), through the irrigation supply line 255*a* in the endoscope shaft 100*a*, and out the irrigation opening 225 at the distal tip 100*c*. The irrigation pump pressure may be calibrated, along with the endoscope irrigation feed and supply lines and external tubing, to deliver a certain range of flow rates of the irrigation fluid.

Figure 4:
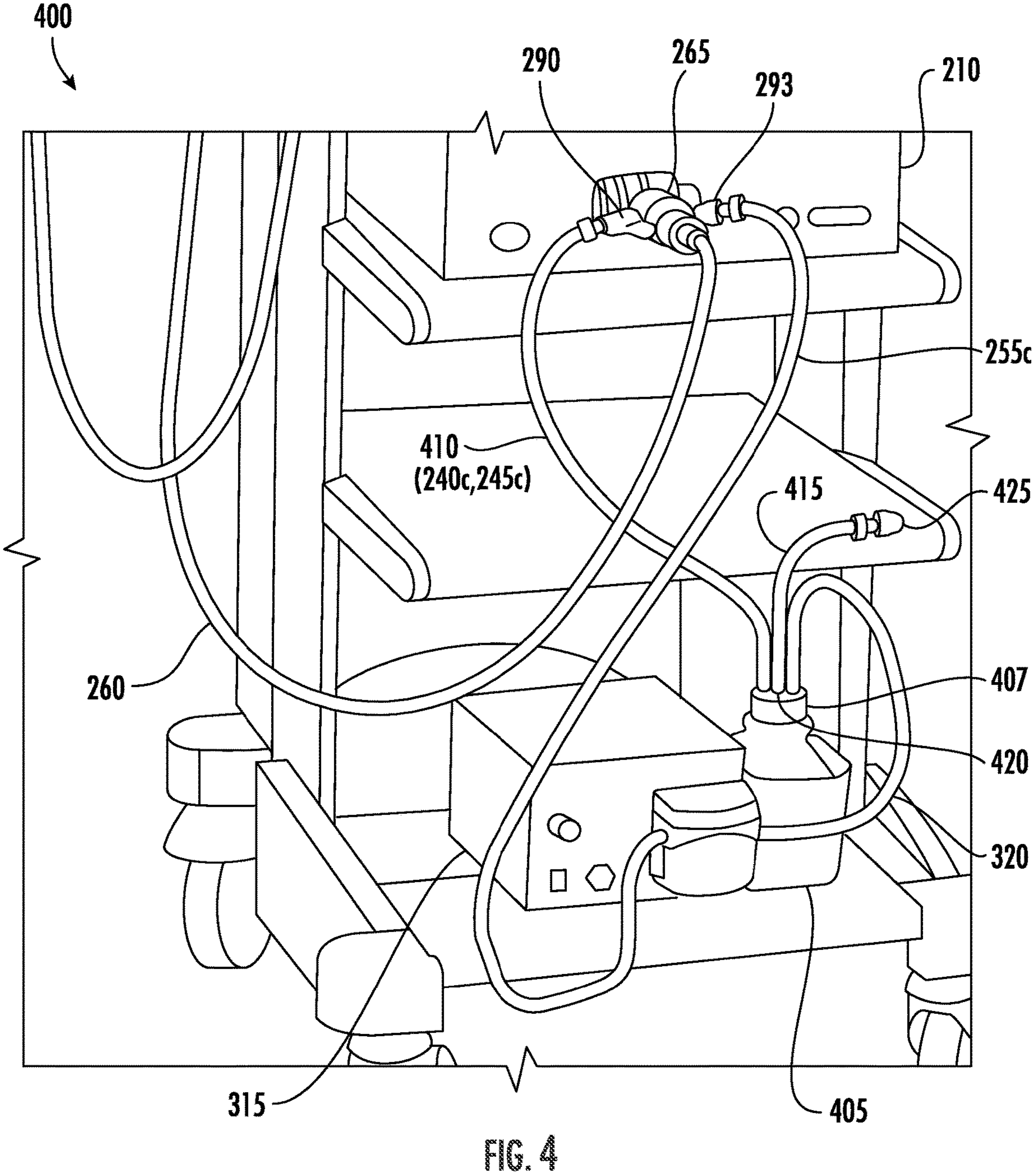
FIG. 4 depicts a hybrid endoscope system including a video processing unit, connector portion, peristaltic irrigation pump, water reservoir and top, coaxial gas and lens wash supply tubing, upstream and downstream irrigation supply tubing, and alternative gas supply tubing.

FIG. 4 is a schematic drawing illustrating a further embodiment of a hybrid system 400 including a video processing unit 210, connector portion 265, peristaltic irrigation pump 315, water reservoir 405 and top 407, coaxial gas and lens wash supply tubing 410, upstream and downstream irrigation supply tubing 320, 255*c* (e.g., first and second lengths of tubing), and alternative gas supply tubing 415 (e.g., $CO_2$). A length of the alternative gas supply tubing 415 passes from one end positioned in the gas gap 275 between the top 407 of the water reservoir 405 and the remaining water 285 in the reservoir through an additional opening 420 in the top 407 of the reservoir 405 to a detachable connection 425 for a source of the alternative gas supply (e.g., hospital house gas source of $CO_2$). When the alternative gas supply is desired, such as $CO_2$ gas, the air pump 215 on the video processing unit 210 may be turned off and $CO_2$ gas, rather than air, is thereby flowed to the water reservoir 405 pressurizing the water surface. In the neutral state, $CO_2$ gas flows backward up the gas supply tubing 240*c* to the connector portion 265, up the gas feed line 240*b*, and is vented through the gas/water valve 140 to atmosphere. In the first position, the user closes off the vent hole in the gas/water valve 140, and the $CO_2$ gas is flowed through the gas/water valve to the gas supply line 240*a* in the endoscope shaft 100*a* and out the gas/lens wash nozzle 220 at the distal tip 100*c*. In the second position, the user depresses the valve 140 to the bottom of the valve location 135, keeping the vent hole in the gas/water valve closed off. The second position blocks the $CO_2$ gas supply to both atmosphere and the gas supply line 240*a* in the endoscope 100, and opens up the gas/water valve 140 to allow lens wash water to pass through to the lens wash line 245*a* (e.g., a supply line) in the endoscope shaft 100*a* and out the gas/lens wash nozzle 220 at the distal tip 100*c*. Gas (pressure) in the reservoir 405 is maintained by delivery gas through alternative gas (e.g., $CO_2$) supply tubing 415. The irrigation function may be accomplished in a similar manner as the operation described above with respect to FIG. 3D.

As discussed above, water for lens wash and/or irrigation may be provided to an endoscope from a water bottle (e.g., 1000 milliliter (ml) disposable, rigid sterile irrigation water bottle or other suitable water bottle) and a hybrid tube set. In some cases, the hybrid tube set may thread to the top of the water bottle and transport water from the water bottle to an endoscope umbilical. Such a water bottle and hybrid tube set may be prone to contamination as the bottle is typically replaced when emptied, which opens up the possibility of the components of the hybrid tube set becoming contaminated. Additionally, due to a threaded connection between many tube sets and water bottles, the system may leak when the tube set is incorrectly threaded onto the water bottle. Further, the water bottle is required to be set on a level surface and level surfaces may be limited in a procedure room.

An option that addresses at least some of the issues when a water bottle is utilized for a water source is to use a hybrid tube set that couples to bag type (e.g. intravenous (IV) bags) sterile irrigation solution bags rather than bottles. Bags of procedure liquid may be available in a myriad of different sizes ranging from 500 ml to 3,000 ml or larger and may be readily available (e.g., available off-the-shelf) at procedure locations (e.g., hospitals, ambulatory surgery centers (ASC), etc.), which may reduce the need to replace a water source throughout a procedure. Further, the bags may be hung on a side of cart or elsewhere in a procedure room rather than needing to be set on a level surface like a bottle. Additionally, connecting a tube set with bag of liquid may utilize a bag spike port rather than a threaded cap, which may reduce leakage opportunities.

Example devices, systems, and methods to supply fluids to an endoscope which may be accessed at a base of a fluid container, including bags and bottles, are described in U.S. Patent Appl. No. 63/419,900, filed on Oct. 27, 2022, and titled DEVICES, SYSTEMS, AND METHODS TO SUPPLY FLUIDS TO AN ENDOSCOPE, which is hereby incorporated by references in its entirety for any and all purposes.

As described above, it may be desirable to reduce opportunities for contamination to the tube set 240*c*, 245*c*, 320, 410, 415 during replacement of the water reservoir(s). An example system that may be configured to reduce opportunities for contamination may include utilizing a container for fluid that may be hung (e.g., a hanger, hook, and/or other suitable hanging mechanism) on or proximate to an endoscope system, that does not require use of a fluid container in communication with a hung container, and to which a tube set providing fluid to an endoscope may connect. Rather than use a fluid container to which a tube set may connect, a fluid supply system may utilize a manifold that connects to the tube set and to a fluid container via a spike port, quick connect, a threaded luer, and/or other suitable fluid container coupling mechanism to conduct fluid from the primary fluid container to the manifold. In some cases, the manifold may have a single connection point with the fluid container, but this is not required. Once fluid from the fluid container enters the manifold, the fluid may flow through the manifold to tubing sets and to an irrigation pump, the fluid may flow to an umbilicus of an endoscope for lens wash and insufflation, and/or the fluid may flow to one or more other components or systems.

The manifold may include one or more fluid pathways for the fluid received therein to travel. In some cases, the fluid may travel along a fluid pathway within the manifold to an irrigation pump or system. Additionally or alternatively, fluid may travel along a fluid pathway into a chamber of the manifold configured to deliver fluid to the umbilicus of the endoscope.

Figure 5:
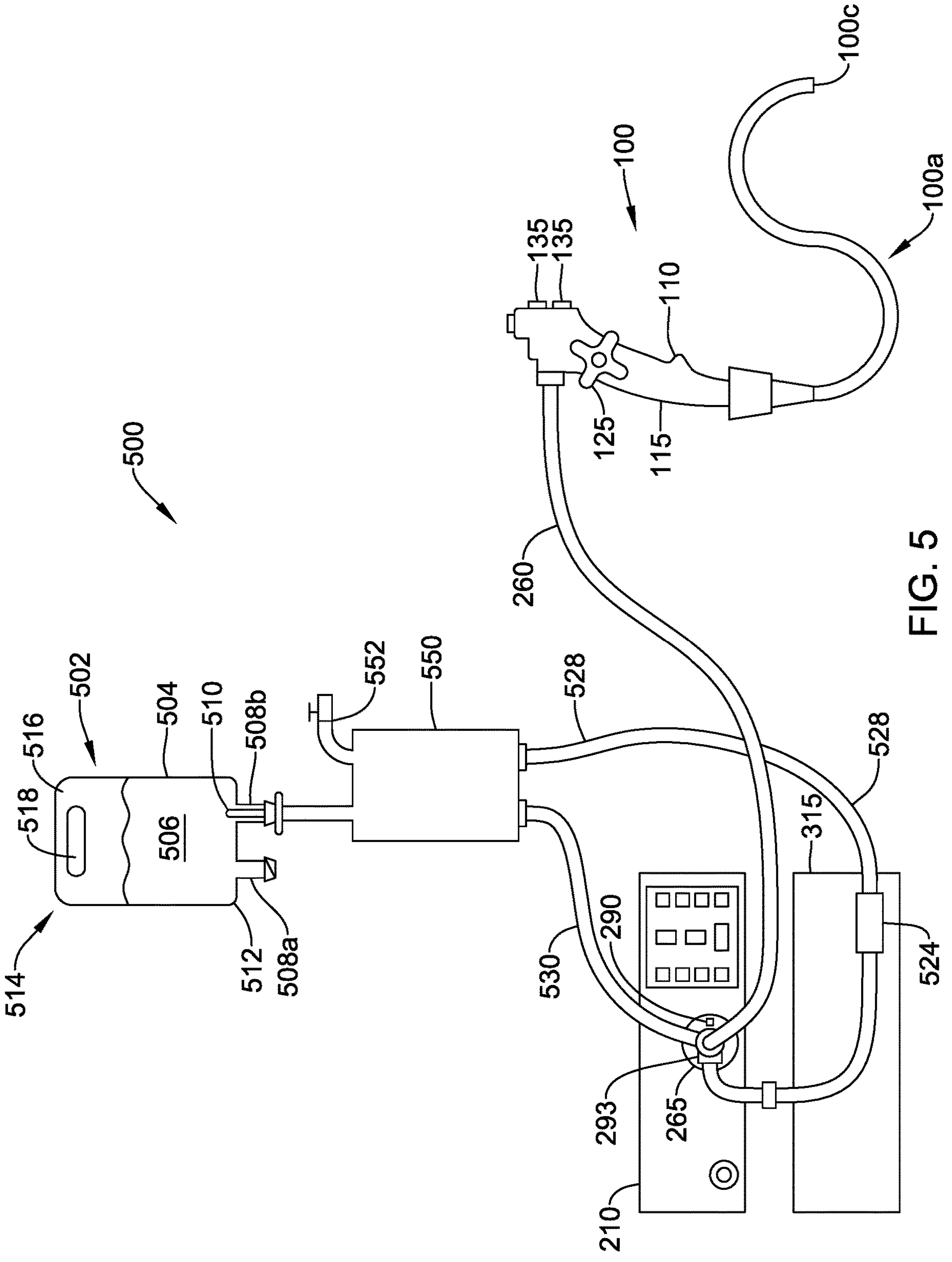
FIG. 5 depicts a schematic view of an illustrative endoscope system.

FIG. 5 depicts a schematic view of an illustrative endoscopic system 500 which may reduce the number of water reservoir changes and/or reduce opportunities for contamination during replacement of the water reservoir(s) relative to fluid delivery systems utilizing bottles as fluid reservoirs and/or using tubing sets coupled directly to a fluid reservoir. The system 500 may include components similar to the endoscope and endoscope systems described with regard to FIGS. 1-4; however, not all features may be described or shown here.

The system 500 of FIG. 5 depicts an illustrative fluid reservoir 502 that may include a container 504 configured to hold a fluid 506. In the illustrated configuration, the container 504 may be fluidly coupled to the upstream irrigation tubing 528 configured to provide fluid for irrigation to the endoscope 100. Generally, the irrigation tubing 528 may be a water or fluid supply line or tube for supplying water or other fluid to an endoscope 100. Alternatively or additionally, the container 504 may be coupled to a gas and lens wash supply tubing 530 to provide insufflation and fluid for clearing the lens. Further, in some cases, the reservoir 502 may supply fluid for both irrigation and lens wash. While not explicitly shown, the reservoir 502 may include printed lines, numbers, or other visual indicia to allow a user to easily determine how much fluid is left in the reservoir 502.

The container 504 may be formed from one or more layers of a lightweight, flexible material, such as, but not limited to, low density polyethylene (LDPE), thermoplastic polyurethane (TPU), silicone, polyethylene terephthalate (PET), aluminum, nylon, polyethylene (PE), plasticized polyvinyl chloride (PVC), or combinations thereof, etc. In some embodiments, the container 504 may be entirely translucent, entirely opaque, or combinations thereof. In some cases, the container 504 may be a flexible bag analogous to those utilized to deliver intravenous replacement fluid in clinical settings (for example, an intravenous (IV) fluid bag). Such bags may be readily available and familiar to the clinician as they are widely used in various sizes. The volume of the container 504 may be variable. For example, the volume of the container 504 may be 500 milliliters (mL) or greater, 1000 mL or greater, 2000 mL or greater, 3000 mL, 4000 mL or greater, etc. The volume may be less than 500 mL or greater than 4000 mL, as desired. The reservoir 502 may be pre-filled (e.g., prior to entering the procedure suite or at the time of manufacturing) with water or other fluid.

In some cases, the clinician may select the reservoir 502 from a plurality of differently sized available reservoirs based on the number and/or types of procedures expected for a day. By selecting a reservoir 502 having a volume large enough to accommodate an entire day of procedures, the need for replacing the sterile fluid source (e.g., the reservoir 502) may be reduced or eliminated. It is contemplated that flexible bags may utilize less plastic (or other material) than a bottle designed to hold a similar amount of fluid. Thus, the use of a flexible bag as a fluid reservoir 502 may increase the level of environmental sustainability of the system 500. For example, if the user sets up the system with a 3000 mL (3 liter) bag reservoir 502 and therefore does not need to utilize three individual one liter bottles, a significant reduction of waste may be realized. It is further contemplated that when disposed of or discarded, a bag reservoir 502 may occupy less volume than a bottle capable of holding an equivalent amount of fluid.

The reservoir 502 may further include one or more ports 508*a*, 508*b*, such as, but not limited to a spike port, a septum port, luer port, etc. extending from and in selective fluid communication with an interior of the container 504. While the reservoir 502 is illustrated as including two ports 508*a*, 508*b*, the reservoir 502 may include one port or more than two ports, as desired. In some cases, at least one port 508*b* may be configured to be in fluid communication with the irrigation tubing 528 and/or the lens wash supply tubing 530, while the other port 508*a* may be configured to allow the user to add additives to the fluid 506 (e.g., pressurized air, pressurized carbon dioxide ($CO_2$), irrigation fluid, etc.)

The ports 508*a*, 508*b* may be formed as a monolithic structure with the first container 504, but this is not required. In some cases, the ports 508*a*, 508*b* may be generally tubular structures with each port 508*a*, 508*b* defining a lumen extending therethrough. The lumens of the ports 508*a*, 508*b* may be configured to selectively fluidly couple the interior of the container 504 with another component, such as, but not limited to, a water or fluid supply tube. In some configurations, the ports 508*a*, 508*b* may be positioned adjacent to a bottom end 512 of the reservoir 502. However, this is not required and one or more of the ports 508*a*, 508*b* may be positioned in other locations, as desired. If the ports 508*a*, 508*b* are positioned at a location other than the bottom end 512 of the container 504, a dip tube or tube extension may be required to access the fluid at the bottom of the container 504.

While not explicitly shown, the ports 508*a*, 508*b* may each include a removable cap or seal configured to form a fluid tight seal with the port 508*a*, 508*b*. The removable cap or seal may help to maintain the sterility of the ports 508*a*, 508*b*. Once the cap or seal has been removed, the port 508*a*, 508*b* may be pierced with a spike tip or spike port adaptor 510 that is coupled to the upstream irrigation tubing 528. For example, in addition to the removable cap or seal, the port 508*a*, 508*b* may include an internal seal disposed within a lumen of the port 508*a*, 508*b* that may be punctured or pierced by the spike port adaptor 510.

The outer surface of the spike port adaptor 510 may form an interference fit with the inner surface of the port 508*a*, 508*b*. The fit and/or coupling between the spike port adaptor 510 and the port 508*a*, 508*b* may be sufficient to remain in place when the port 508*a*, 508*b* is in fluid communication with the irrigation supply tube 528, the lens wash supply tube 530, and/or other tubing sets.

The reservoir 502 may include a handle 516 positioned adjacent to a top portion 514 thereof. The handle 516 may define an opening or through hole 518 for receiving a hand or hook therethrough to carry or hold the reservoir 502. The handle 516 may allow the reservoir 502 to be hung from a hook, such as, but not limited to an IV stand. Hanging the reservoir 502 may allow the reservoir 502 to be positioned above the level of an endoscope cart which may enable the user to see the fluid 506 level at any time. This may help the clinician avoid running out of fluid during a procedure. Additionally, elevating the reservoir may eliminate the need for the clinician to bend or stoop during setup of the system 500 and/or to change the reservoir 502. In some cases, head pressure generated from the elevating the reservoir 502 may enable rapid priming of the irrigation circuit (and/or lens wash circuit if so connected) which may save time during setup. It is further contemplated that hanging the reservoir 502 from a hook or IV stand may allow the reservoir 502 to be positioned away from expensive capital equipment thus reducing or eliminating the potential for fluid running or flowing inadvertently onto the capital equipment and causing damage or destruction.

The reservoir 502 may be in fluid communication with a lumen of the irrigation supply tube 528, as discussed. The irrigation supply tube 528 may be positioned at or through a pump head 524 of the peristaltic irrigation pump 315 or other suitable pump system. From the pump 315, the irrigation supply tube 528 may fluidly couple with an irrigation lumen of the endoscope 100.

In some configurations, the irrigation pump 315 may be omitted. For example, the reservoir 502 may be inserted into a compression sleeve. When irrigation fluid is desired, the compression sleeve may be activated to exert pressure on an outer surface of the reservoir 502 and to provide the required pressure to perform irrigation at the distal end of the endoscope 100.

A lens wash supply tubing 530 may be in fluid communication with the first port 508*a*. Fluid from the lens wash supply tubing 530 may be provided to the endoscope 100 directly or indirectly, such as, for example, via the umbilical 260, as depicted in FIG. 5. In some cases, lens wash supply tubing 530 may be a dual lumen (e.g., coaxial dual lumen, parallel dual lumen, etc.) tubing set with one lumen for passing gas and another lumen for passing liquid. The lens wash supply tubing 530 may be in fluid communication with the same reservoir 502 with which the irrigation supply tubing 528 is in fluid communication, but this is not required.

In some cases, the reservoir 502 may be releasably and/or permanently fluidly coupled to a manifold 550 via one of the ports 508*a*, 508*b*. The manifold 550 may also be releasably or permanently fluidly coupled the irrigation tubing 528 and the lens wash supply tubing 530. The manifold 550 may be configured to receive pressurized gas (e.g., from the endoscope processor, pump, and/or other suitable source) via a lumen of the lens wash supply tubing 530 and provide liquid from the reservoir 502 to the irrigation tubing 528 and the lens wash supply tubing 530. In some cases, the pressurized gas received at the manifold may be utilized by the manifold to provide liquid to a lumen of the lens wash supply tubing 530.

The manifold 550 may include one or more auxiliary ports (e.g., an auxiliary port 552, as depicted in FIG. 5). The auxiliary port 552 may be configured to receive a pressurized gas (e.g., $CO_2$ and/or other suitable pressurized gas) that may be utilized in addition to or as an alternative to a pressurized gas received via the lens wash supply tubing 530 and/or used for insufflation at the endoscope 100.

If there is a need to replace the reservoir 502 with a new full bag, for example when the reservoir 502 is empty or near empty, the user may, optionally, hang the new bag near the reservoir 502 to be replaced. The user may then disengage the spike port adaptor 510 from the port 508*b* and insert the spike port adaptor 510 into a port of the new bag. This may be performed without requiring the clinician to bend or stoop to access the reservoir 502. The port 508*b* may self-seal to prevent fluid leaks from the reservoir 502 as it is being replaced or upon removal of the spike port adaptor 510. This method of replacing the reservoir 502 may have a lower risk of introducing contaminants into the systems relative to traditional bottle systems. For example, the change out method described herein may allow the reservoir 502 to be changed out without having tubing tangling from a cap (as in a bottle system). Further, the system 500 may remain largely closed as the reservoir 502 is changed out.

Figure 6:
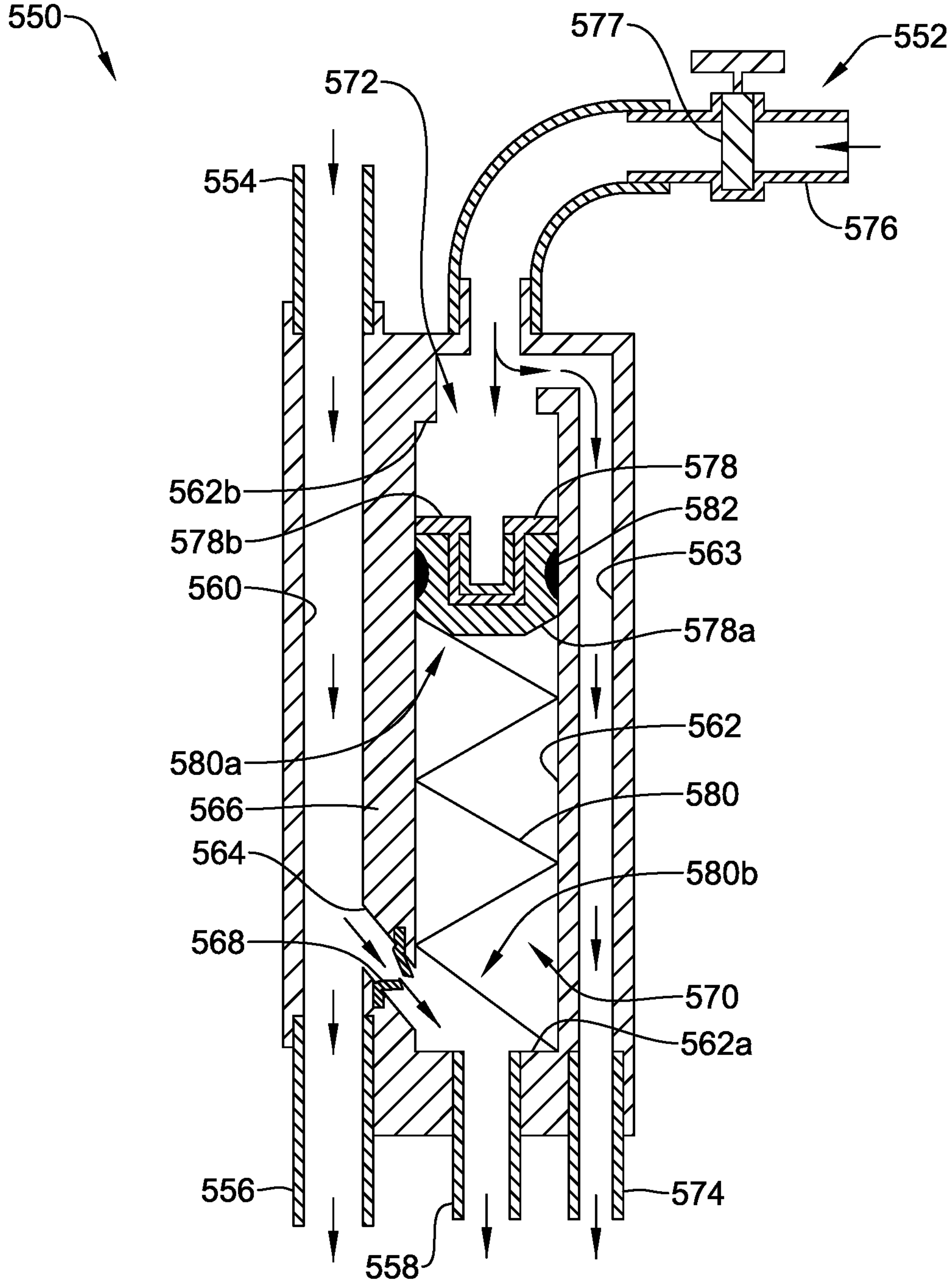
FIG. 6 depicts a schematic cross-section view of an illustrative manifold for use with an endoscope system, the manifold includes an adjustable divider in a first position.
Figure 7:
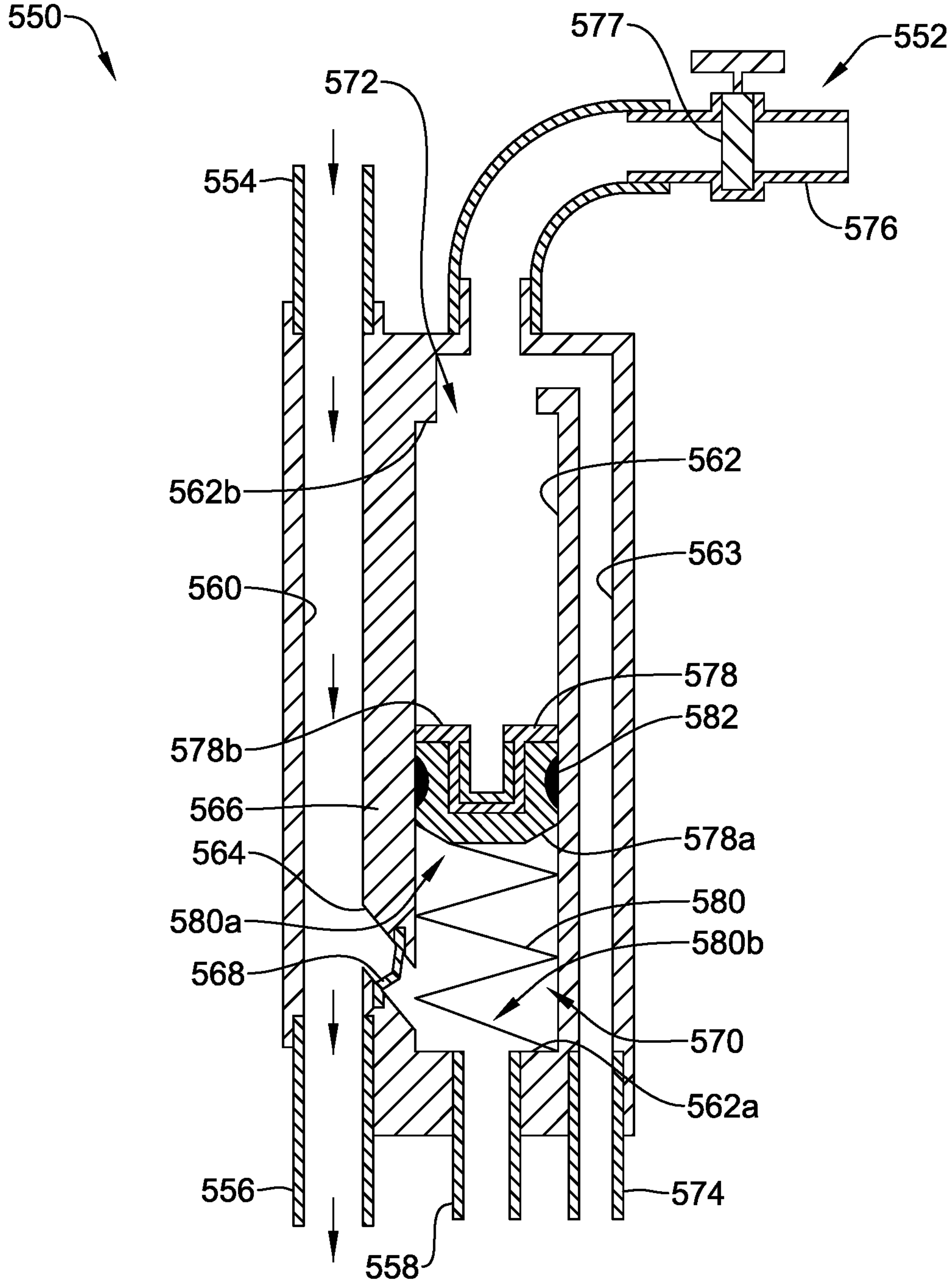
FIG. 7 depicts a schematic cross-section view of the illustrative manifold depicted in FIG. 6, with the adjustable divider in a second position.

FIGS. 6 and 7 depict schematic cross-sectional views of an illustrative configuration of the manifold 550 including one or more ports. Among other ports, the manifold 550 may include a first input port 554 (e.g., a liquid input port or a fluid inlet), a first output port 556 (e.g., a first fluid outlet), and a second output port 558 (e.g., a second fluid outlet). In some cases, one or more conduits may be configured to receive fluid from the first input port 554 and transport the fluid to the first output port 556 and/or the second output port 558.

The manifold 550 may include one or more conduits. In one example, the manifold 550 may include a first conduit 560 (e.g., a first fluid pathway or irrigation conduit), a second conduit 562 (e.g., a second fluid pathway), and a third conduit 563 (e.g., a pressurized gas pathway), but other suitable number of conduits are contemplated. As depicted in FIG. 6, the first conduit 560 may extend between the first input port 554 and the first output port 556, the second conduit 562 may extend between the second output port 558 and an outlet of the third conduit 563, and the third conduit 563 may extend between the first gas input port 574 and an inlet to the second conduit 562.

The one or more conduits of the manifold 550 may be any suitable shape and/or size. For example, the conduits may be elongated, be cylindrical, have a square cross-section, have a rectangular cross-section, have a star cross-section, have an elliptical cross-section, and/or have other suitable shapes and/or sizes.

The first input port 554 may be coupled (e.g., mechanically and/or fluidly coupled) to a liquid reservoir (e.g., the reservoir 502 and/or other suitable reservoir as discussed herein or otherwise) from which the manifold 500 may receive liquid. In one example, liquid from the liquid reservoir may flow into the first input port 554 as a result of gravity acting on the liquid and/or in response to a pressure change within the manifold 550.

Fluid entering the first input port 554 may flow through the first conduit 560 to the first output port 556 to an irrigation tubing set (e.g., irrigation tubing as discussed herein and/or otherwise) coupled thereto and to an irrigation pump (e.g., a peristaltic pump or other suitable pump). Additionally or alternatively, fluid entering the first input port 554 may flow through the first conduit 560 and into the second conduit 562 (e.g., a compressible chamber, a lens wash conduit, and/or other suitable conduit).

In some cases, fluid passing through the first conduit 560 may be shunted through a channel or passageway 564 in a wall 566 of the manifold 550 separating the first conduit 560 and the second conduit 562. Although the passageway 564 is depicted as being an angle in a direction of flow (e.g., as represented by the arrows in the first conduit 560), this is not required and the passageway 564 may be at one or more other suitable angles relative to the direction of fluid flow, the first conduit 560, and/or the second conduit 562. In addition to or as an alternatively to being shunted from the first conduit 560 to the second conduit 562, fluid from the first conduit 560 may be pulled (e.g., selectively pulled) into the second conduit 562 due to pressure differences between the first conduit 560 and the second conduit 562. In some cases, fluid entering the first conduit 560 may be provided to the first output port 556 and the second conduit 562 simultaneously, but this is not required.

In some cases, a valve 568 may be positioned between the first conduit 560 and the second conduit 562. The valve 568 may be a one-way or check valve and/or other suitable valve configured to allow fluid to pass or flow from the first conduit 560 to the second conduit 562 (e.g., to a compressible chamber of the second conduit 562) and block or prevent fluid from passing to the first conduit 560 from the second conduit 562 (e.g., from the compressible chamber of the second conduit 562). In one example configuration, the valve may be a duck-bill valve, as depicted in FIG. 6.

The manifold 550 may include one or more chambers. For example, the manifold 550 may include a first chamber 570 (e.g., a lens wash chamber) and a second chamber 572 configured to adjust in size relative to one another. In one example, the first chamber 570 may be a compressible chamber and the second chamber 572 may be a pressurized chamber, such that when the second chamber 572 is pressurized, a volume of the second chamber 572 expands and a volume of the first chamber 570 may be reduced or compressed, as depicted in FIG. 7. As depicted in FIGS. 6 and 7, the second conduit 562 may include the first chamber 570 and the second chamber 572, but this is not required in all configurations.

In some cases, the first chamber 570 may receive fluid from the passageway 564 via the valve 568 and output fluid through the second output port 558 to lens wash tubing or other suitable tubing. In one example, the first chamber 570 may be expanded (e.g., enlarged) to facilitate drawing fluid into the first chamber 570 from the first conduit 560 and through the passageway 564. The first chamber 570 may then be compressed (e.g., reduced in size) to facilitate outputting fluid to or through the second output port 558.

The second chamber 572 may be in fluid communication with the third conduit 563, which may be in fluid communication with a first gas input port 574 and/or a second gas input port 576 (e.g., the auxiliary port 552 coupled to a $CO_2$ source and/or other suitable gas input port) configured to receive pressurized or compressed gas in response to a lens wash function being activated at the endoscope (e.g., a lens wash button being pressed). In response to receiving pressurized or compressed gas through one or both of the first gas input port 574 and the second gas input port 576, a pressure in the second chamber 572 may increase and cause the first chamber 570 to compress to a second volume from a resting, first volume and, in response, fluid to exit the first chamber 570 via the second output port 558 to lens wash tubing.

The first and second chambers 570, 572 may have suitable initial or first volumes. In one example, the respective initial volumes of the first and second chambers 570, 572 may be determined based on a volume of liquid desired in response to a call for lens wash liquid at the endoscope, but this is not required.

The first gas input port 574 and the gas input port 576 may be configured to receive any suitable pressurized or compressed gas. In one example, the first gas input port 574 may be configured to receive pressurized air from a processor, air pump, or other pressurized air source of the endoscope system in fluid communication with an insufflation tube to an endoscope. Additionally or alternatively, the second gas input port 576 may be in fluid communication with a source of carbon dioxide ($CO_2$). When the second input port 576 is included and is configured to receive $CO_2$, received $CO_2$ may pressurize the second chamber 572 and, optionally, may pass through the third conduit 563 to provide insufflation at the endoscope. Other suitable configurations are contemplated.

The second gas input port 576 may include an adjustable valve 577. The adjustable valve 577 may be any suitable type of valve including, but not limited to, a one-way or check valve, an active valve that is operated in a binary manner as an on/off valve or switch to allow flow to be turned on or allow flow to be turned off (e.g., a stopcock valve, solenoid valve, peristaltic pump, blow off valve), a valve that can be adjusted to positions between a fully closed and a fully open position, and/or other suitable type of valve. In one example, the adjustable valve 577 may be or may include a stopcock.

In some cases, there may be an adjustable barrier or divider 578 between the first chamber 570 and the second chamber 572. The adjustable divider 578 may be configured to adjust positions and, as a result, adjust respective volume sizes of the first chamber 570 and the second chamber 572 in response to changes in forces acting on the adjustable divider 578 (e.g., forces from pressures in the first and second chambers 570, 572, forces from a biasing member 580, and/or other suitable forces acting on the adjustable divider 578). The adjustable divider 578 may include or be used with a biasing member 580.

The adjustable divider 578 may be any suitable type of divider configured to adjust relative to the second conduit 562. For example, the adjustable divider 578 may be a flexible membrane, a diaphragm, a plunger, a seal, and/or other suitable adjustable divider. In one example, the adjustable divider 578 may be a plunger with one or more seals 582 (e.g., an O-ring, a resilient material of the plunger, etc.) extending around the adjustable divider 578, as depicted in FIG. 6, to create a fluid-tight seal between the adjustable divider 578 and a wall of the second conduit 562. Other configurations of the adjustable divider 578 are contemplated.

The adjustable divider 578 maybe formed from one or more materials. In one example, the adjustable divider 578 may be a plunger formed from a rigid first material facing the first chamber 570 and/or the second chamber 572 and a flexible and/or resilient second material (e.g., a seal) configured to engage and seal against a wall or walls of the second conduit 562, but this is not required. In another example, the adjustable divider 578 may be a diaphragm made from a flexible and/or resilient material.

The biasing member 580 may be any suitable member and/or material configured to bias the adjustable divider 578 to a first position (e.g., a resting position) in the second conduit 562 such that first chamber 570 has the first volume and the second chamber 572 has a first volume. For example, biasing member 580 may be a spring, a flexible, resilient material of the adjustable divider 578, and/or other suitable biasing member. In one example, the biasing member 580 may be a compression spring, as depicted in FIG. 6. When the biasing member 580 is a spring, a first end 580*a* of the biasing member 580 may engage a first side 578*a* of the adjustable divider 578 and a second end 580*b* of the biasing member 580 may engage a first surface 562*a* transverse to a longitudinal axis of the second conduit 562 to bias a second side 578*b* of the adjustable divider 578 toward a second surface 562*b* of the second conduit 562. In some cases, the biasing member 580 may be omitted and addition of gas to the second chamber 572 may cause the adjustable divider 578 to adjust in a first direction to cause fluid to exit the first chamber 570 and withdrawal of gas from the second chamber 572 may cause the adjustable divider 578 to adjust in a second direction opposite the first direction and create a negative pressure in the second conduit 562 to cause fluid to enter the first chamber 570 via the passageway 564.

In operation, when a user calls for lens wash fluid at the endoscope (e.g., by activating a lens wash button and/or in one or more other suitable manners), pressurized or compressed gas may enter the second chamber 572 and cause the adjustable divider 578 to adjust from the first position (e.g., a resting position) to a second position (e.g., a pressurized position) in response to the pressurized or compressed gas causing a pressure in the second chamber 572 to overcome the bias of the biasing member 580 and increase a volume of the second chamber 572 (e.g., to a second volume (e.g., a pressurized volume)), compress or decrease a volume of the first chamber 570 (e.g., from the first volume to a second volume (e.g., a pressurized volume)), and push liquid out of the first chamber 570 via the second output port 558, as shown in FIG. 7 relative to FIG. 6, to lens wash tubing fluidly coupled with an endoscope. When the user stops the call for lens wash fluid at the endoscope (e.g., deactivating the lens wash button and/or in one or more other suitable manners), pressurized gas is no longer provided to the second chamber 572 and the bias member 580 may force the adjustable divider 578 from the second position to the first position, which may pull fluid into the first chamber 570 from the first conduit 560 via the passageway 564 due to a vacuum pressure caused by the movement of adjustable divider 578 to the second position, forces in the first conduit 560, gravity, and/or other forces acting the on fluid received at the first input port 556, such that the first chamber 570 is refilled with lens wash liquid and is ready for the next lens wash cycle.

Figure 8:
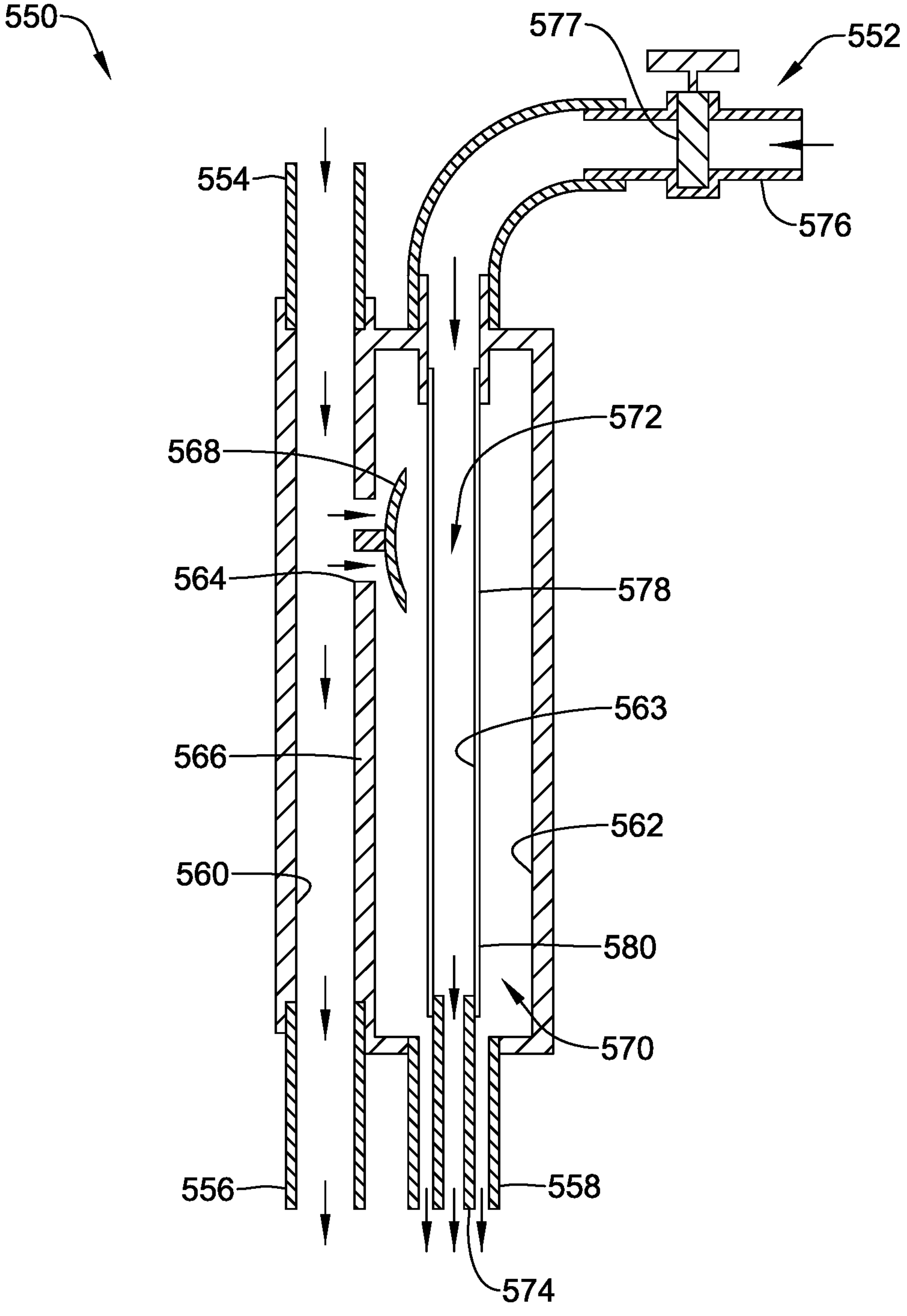
FIG. 8 depicts a schematic cross-section view of an illustrative manifold for use with an endoscope system, the manifold includes an adjustable divider in a first position.
Figure 9:
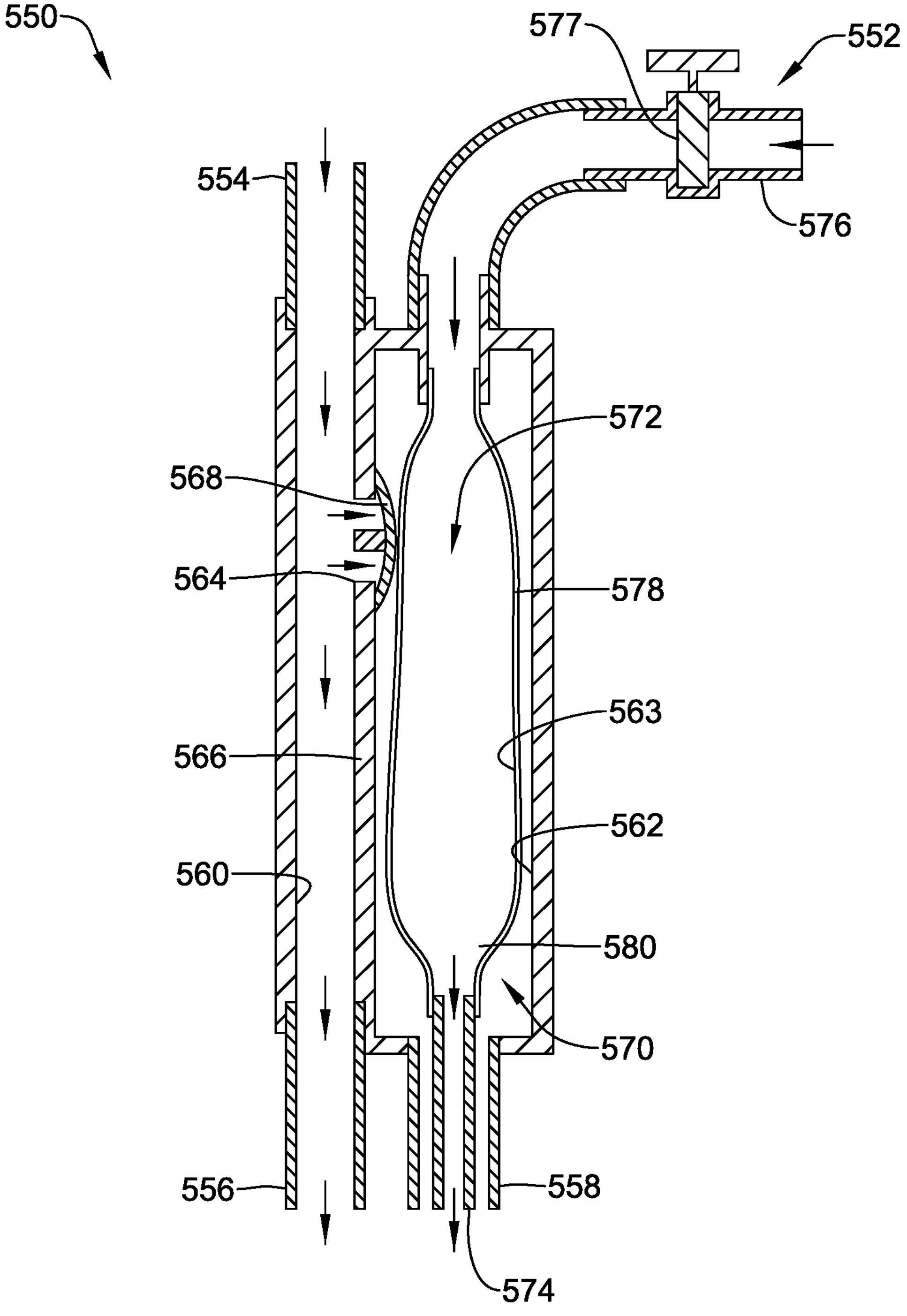
FIG. 9 depicts a schematic cross-section view of the illustrative manifold depicted in FIG. 8, with the adjustable divider in a second position.

FIGS. 8 and 9 depict a schematic cross-sectional view of an illustrative configuration of the manifold 550 including the first input port 554 (e.g., a fluid inlet), the first output port 556 (e.g., a first fluid outlet), and the second output port 558 (e.g., a second fluid outlet), where the adjustable divider 578 may be or may include a diaphragm. The adjustable divider 578 may extend between the second conduit 562 and the third conduit 563 such that the second conduit 562 may define or include the first chamber 570 and the third conduit 563 may define or include the second chamber 572, as depicted in FIGS. 8 and 9.

Similar to as discussed above with FIGS. 6 and 7, a portion of the fluid entering the first input port 554 may flow through the first conduit 560 to the first output port 556 to an irrigation tubing coupled thereto and to an irrigation pump and a portion of the fluid entering the first input port 554 may flow through the first conduit 560 and into the second conduit 562. In some cases, fluid passing through the first conduit 560 may be shunted through the channel or passageway 564 in the wall 566 of the manifold separating the first conduit 560 and the second conduit 562. In addition to or as an alternatively to being shunted from the first conduit 560 to the second conduit 562, fluid from the first conduit 560 may be pulled (e.g., selectively pulled) into the second conduit 562 due to pressure differences between the first conduit 560 and the second conduit 562.

In some cases, the passageway 564 may include a valve 568 configured to allow fluid to pass from the first conduit 560 to the second conduit 562 and prevent fluid moving from the second conduit 562 to the first conduit 560 via the passageway 564. The valve 568 may be an umbrella valve, as depicted in FIGS. 8 and 9, and/or one or more other suitable types of valves as discussed herein or otherwise.

The second conduit 562 and the third conduit 563 may include one or more shared walls. In one example, the second conduit 562 may be concentric about the third conduit 563, as depicted in FIGS. 8 and 9. When the second conduit 562 is concentric about the third conduit 563, the second output port 558 and the first gas inlet 574 may be configured to couple with a concentric, dual lumen lens wash tubing set, where the inner lumen may be a gas lumen configured to bring pressurized gas to (e.g., from a processor of the endoscope system) and/or from (e.g., from a source of $CO_2$) the third conduit 563 and the outer lumen may be a liquid lumen configured to deliver liquid to the endoscope. Alternatively or additionally, the third conduit 563 may be concentric about the second conduit 562 and/or the second conduit 562 and the third conduit 563 may be side-by-side one another.

In some cases, the shared wall(s) between the second conduit 562 and the third conduit 563 may be or may include the adjustable barrier or divider 578. When the adjustable divider 578 is a shared wall, the adjustable divider 578 may be a diaphragm formed from a flexible, resilient, and/or expandable material. Alternatively or additionally, the adjustable divider 578 may be formed from one or more other suitable materials and/or take on one or more configurations including, but not limited to, a flexible divider, a bellows, a balloon, and/or other suitable flexible and/or expandable members configured to displace under positive gas pressure to compress fluid of the first chamber 570. In one example, the adjustable divider 578 may be a diaphragm configured to expand and contract like a balloon.

The adjustable divider 578 depicted in FIGS. 8 and 9 as a shared wall between the second conduit 562 and the third conduit 563 may be configured to expand and contract to change a volume size of the first chamber 570 and the second chamber 572. For example, as the adjustable divider contracts in response to a lack of gas pressure in the second chamber 572, the first chamber 570 (and the second conduit 562) may increase in volume and the second chamber 572 (and the third conduit 563) may decrease in volume to respective resting volumes. In the example, as the adjustable divider expands, the first chamber 570 (and the second conduit 562) may decrease in volume and the second chamber 572 (and the third conduit 563) may increase in volume to respective pressurized volumes.

When the adjustable divider 578 is a diaphragm, the flexible, resilient, and/or expandable material of the adjustable divider 578 may be or may include the biasing member 580 such that the material is configured to bias the adjustable divider 578 to a first position (e.g., a resting position) associated with a first volume (e.g., the resting volume) of the first chamber 570 and draw fluid into the first chamber 570 from the first conduit 560 when adjusting from a second position (e.g., a pressurized position) associated with a second volume (e.g., the pressurized volume) of the first chamber 570 to the first position. Alternatively or additionally, an additional biasing member (e.g., biasing material or structure) may be utilized to bias the diaphragm of the adjustable divider 578. In some cases, the biasing member 580 may be omitted and addition of gas (e.g., $CO_2$ or pressurized air) to the second chamber 572 may cause the adjustable divider 578 to expand and withdrawal of gas from the second chamber 572 may create a negative pressure in the second chamber 572 to cause the diaphragm of the adjustable divider 578 to contract and cause fluid to enter the first chamber 570 via the passageway 564.

In operation, when a user calls for lens wash fluid at the endoscope (e.g., by activating a lens wash button and/or in one or more other suitable manners), pressurized or compressed gas may enter the second chamber 572 (e.g., pressurized air via the first gas inlet 574 or $CO_2$ via the second gas inlet 576) and create a pressure in the second chamber 572 that acts on the adjustable divider 578 and causes the adjustable divider 578 to overcome the bias force thereof to expand from the first position to the second position and compress a volume of the first chamber 570 and push liquid out of the first chamber 570 through the second output port 558, as shown in FIG. 9 relative to FIG. 8, to lens wash tubing fluidly coupled to an endoscope. When the user stops the call for lens wash fluid at the endoscope (e.g., deactivating the lens wash button and/or in one or more other suitable manners), pressurized gas is no longer provided to the second chamber 572 and the bias member 580 of the adjustable divider 578 may force the adjustable divider 578 to the first position, which may pull fluid into the first chamber 570 from the first conduit 560 via the passageway 564 due to a vacuum pressure in the second conduit 562 caused by the movement of adjustable divider 578 to the resting position, forces in the first conduit 560, gravity, and/or other forces acting the on fluid received at the first input port 556, such that the first chamber 570 is refilled with lens wash liquid and is ready for the next lens wash cycle.

Figure 10:
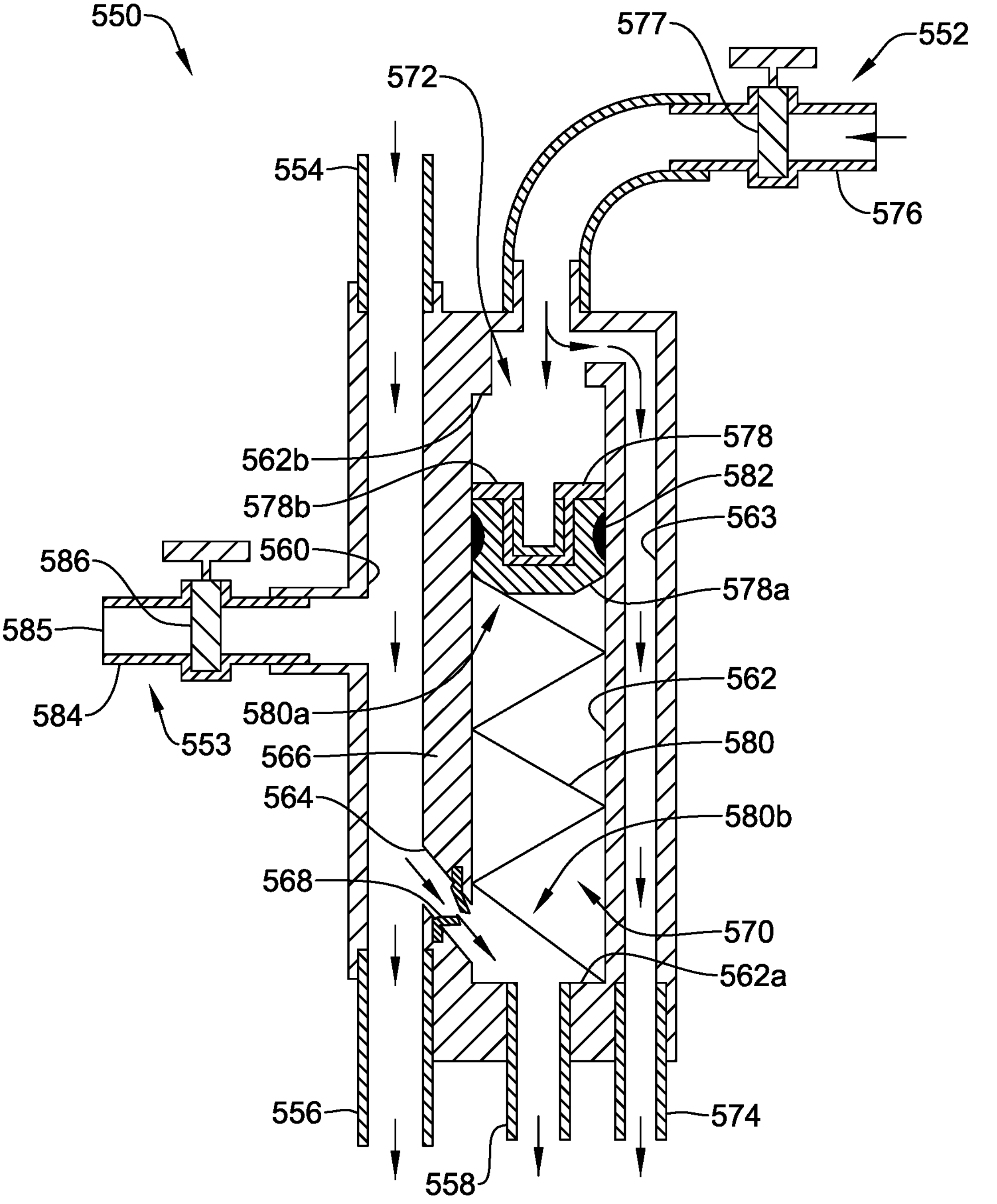
FIG. 10 depicts a schematic cross-section view of an illustrative manifold for use with an endoscope system.

FIG. 10 depicts a schematic cross-sectional view of the manifold 550 with a second auxiliary port 553 (e.g., a third output port 584 or a fluid access port) in fluid communication with the first conduit 560. In some cases, the third output port 584 may be configured as a needless access port to enable a user to access fluid from a fluid source coupled to the first input port 554 with a syringe and/or other suitable device.

The third output port 584 may be any suitable type of port. In one example, the third output port 584 may be "T" style output port extending from the first conduit 560. An access point 585 of the third output port 584 (e.g., a distal end or other suitable portion of the third output port 584) may be or may include a luer fitting, a slip fitting, a septum, a needleless septum valve, a needle septum valve, and/or other suitable connector and/or accessible seal.

The third output port 584 may include an adjustable valve 586. The adjustable valve 586 may be any suitable type of valve including, but not limited to, a one-way or check valve, an active valve that is operated in a binary manner as an on/off valve or switch to allow flow to be turned on or allow flow to be turned off (e.g., a stopcock valve, solenoid valve, peristaltic pump, blow off valve), a valve that can be adjusted to positions between a fully closed and a fully open position, and/or other suitable type of valve. In one example, the adjustable valve 586 may be or may include a stopcock. In another example, the adjustable valve 586 may be or may include a spring-loaded valve with a lever, button, handle, and/or other suitable actuator configured to allow a user to initiate a flow of fluid from the fluid source coupled to the first input port 554 out of the third output port 584.

In some cases, the adjustable valve 586 may be formed as part of the manifold 550. Additionally or alternatively, the adjustable valve 586 may be coupled to the third output port.

Figure 11:
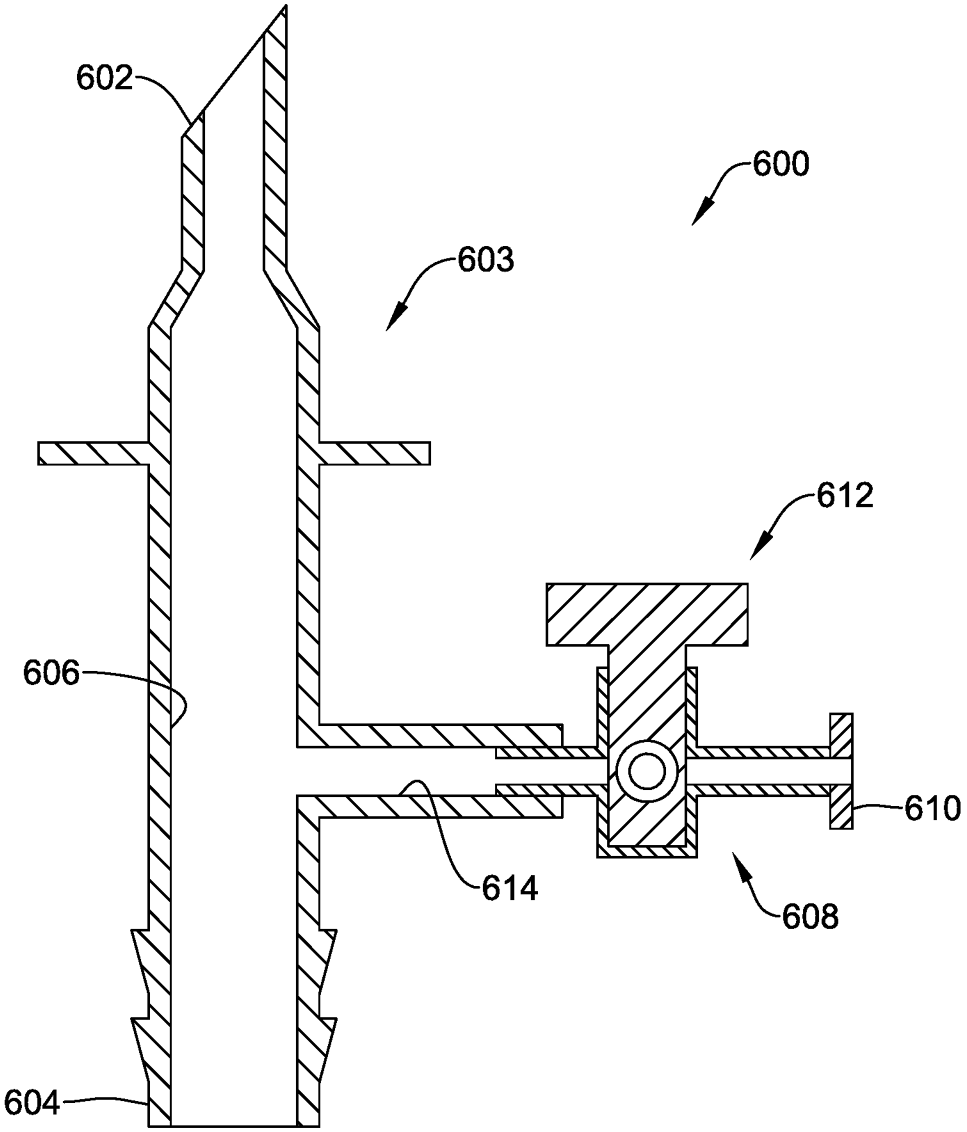
FIG. 11 depicts a schematic cross-section view of an illustrative spike port assembly for use with an endoscope system.

FIG. 11 depicts a schematic cross-sectional view of a spike port assembly 600 having an adjustable output 608 similar to the third output port 584 depicted in FIG. 10. The spike port assembly 600 may include a spike port 602, where the spike port 602 may engage a liquid source (e.g., a bag reservoir and/or other suitable liquid reservoir configured to be accessed with a spike port) and be an input port configured to receive liquid from the liquid source. Further, the spike port 602 may have a seal portion 603 configured to engage with a septum port or other port of the liquid source.

The port assembly 600 may include a tube port 604, where the tube port 604 may be an output port configured to receive liquid from the liquid source passing through the spike port 602 and a first conduit 606 extending between the spike port 602 and the tube port 604. In some cases, the tube port 604 may be barbed, as depicted in FIG. 11, and/or may have other suitable connector features.

The adjustable output port 608 may be any suitable type of port. In one example, the adjustable output port 608 may be a "T" style output port extending from the conduit 606. An access point 610 of the adjustable output port 608 (e.g., a distal end or other suitable portion of the adjustable output port 608) may be or may include a luer fitting, a slip fitting, a septum, a needleless septum valve, a needle septum valve, and/or other suitable connector and/or accessible seal. In one example, the access point 610 may be a luer fitting or connector as depicted in FIG. 11.

The adjustable output port 608 may include an adjustable valve 612. The adjustable valve 612 may be any suitable type of valve including, but not limited to, a one-way or check valve, an active valve that is operated in a binary manner as an on/off valve or switch to allow flow to be turned on or allow flow to be turned off (e.g., a stopcock valve, solenoid valve, peristaltic pump, blow off valve), a valve that can be adjusted to positions between a fully closed and a fully open position, and/or other suitable type of valve. In one example, the adjustable valve 612 may be or may include a stopcock, as depicted in FIG. 11. In another example, the adjustable valve 612 may be or may include a spring-loaded valve with a lever, button, handle, and/or other suitable actuator configured to allow a user to initiate a flow of fluid from the fluid source coupled to the spike port 602 out of the adjustable output port 608.

In some cases, the adjustable valve 612 may be formed as part of the spike port assembly 600. Additionally or alternatively, the adjustable valve 612 may be coupled to a second conduit 614 extending from the first conduit 606, as depicted in FIG. 11.

Figure 12:
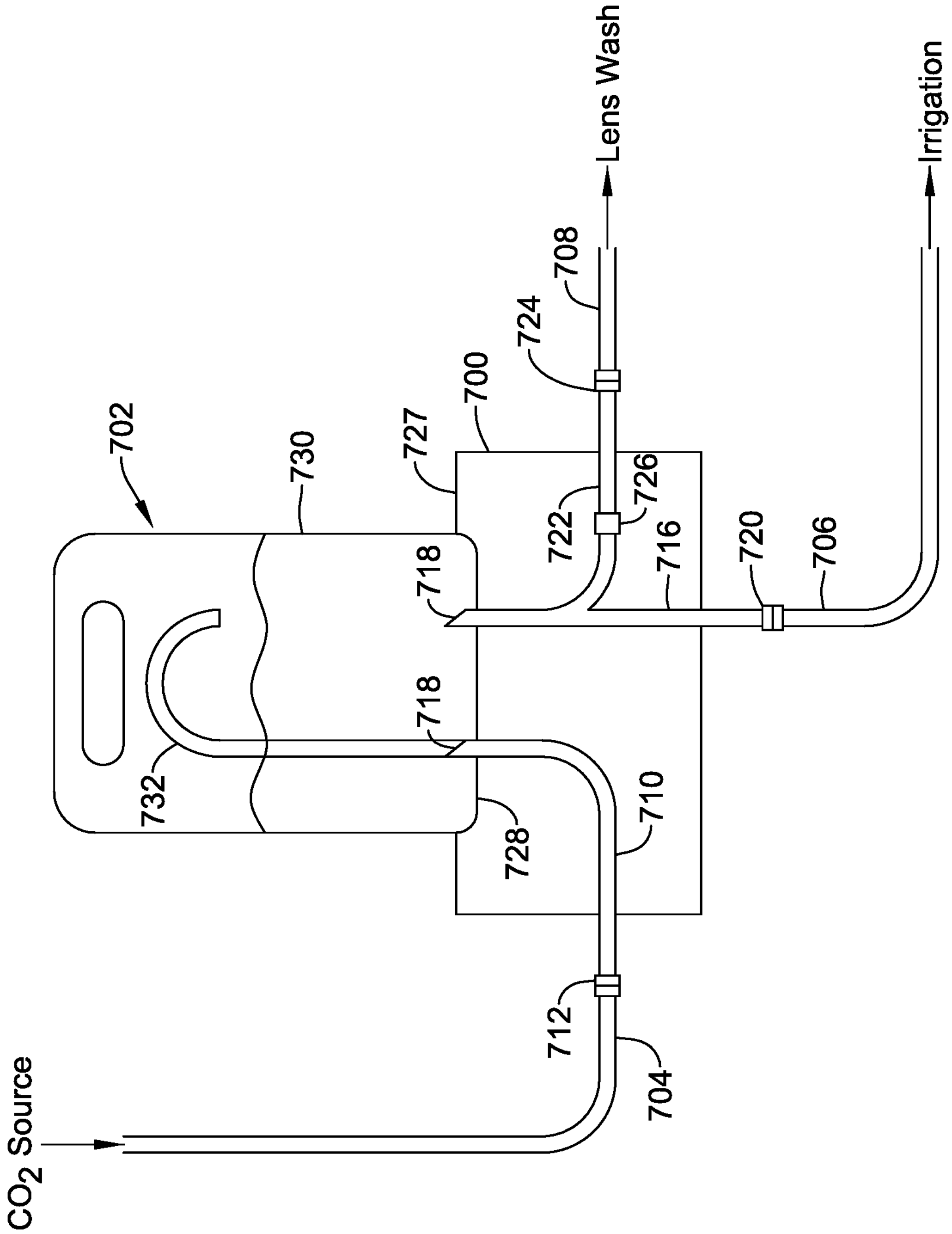
FIG. 12 depicts a schematic view of an illustrative fluid supply assembly for an endoscope system.

FIG. 12 is a schematic view of an illustrative configuration of a fluid supply assembly with a manifold 700 coupled to a fluid source 702 and one or more tubing sets (e.g., a first tubing set 704, a second tubing set 706, a third tubing set 708, and/or other suitable tubing sets). The manifold 700 may be configured with a plurality of connectors configured to couple with a fluid source having a bag configuration and connectors of the one or more tubing sets. In some cases, the manifold may be pre-configured to for use with the liquid source and tubing sets, to allow for quick replacement of the fluid source without requiring disconnection of the tubing sets in fluid communication with the liquid source. The manifold 700 may be configured in a similar and/or different manner to the other manifolds described herein as interfacing a liquid source, pressurized gas, and tubing sets.

The manifold 700 may include a plurality of conduits. As depicted in FIG. 12, the manifold 700 may include a gas conduit 710 extending from a gas input port 712 to a gas output port 714, an irrigation conduit 716 extending from a fluid input port 718 to an irrigation output port 720, and lens wash conduit 722 extending from the fluid input port 718 to the lens wash port 724. Other suitable conduit configurations are contemplated.

The conduits 710, 716, 722 may include one or more valves. In some cases, one or more of the conduits 710, 716, 722 may include a one-way or check valve to prevent back flow of fluid through the conduits 710, 716, 722. In one example, the lens wash conduit 722 may include a one-way or check valve 726, as depicted in FIG. 12.

In some cases, the manifold 700 may include a housing 727 defining the conduits 710, 716, 722 and a recess 728 configured to receive a base port other portion of the liquid source 702. When a container 730 (e.g., a bag or other suitable container) of the liquid source 702 is configured to be used with the manifold 700, the recess 728 may facilitate receiving the manifold 700 and aligning the container 730 of the liquid source 702 with the gas output port 714 and/or the fluid inlet port 718.

In some cases, the gas output port 714 and the fluid input port 718 may extend outward from the recess 728 (e.g., from a surface of the recess 728 and/or from one or more other suitable portion of the recess 728) in a body or housing 727 of the manifold 700. Although not required, the gas output port 714 and/or the fluid input port 718 may be spike ports (e.g., bag spike ports and/or other suitable spike ports) configured to engage spike receiving ports on the container 730 with a press fit as the container 730 is positioned at or within the recess 728. In some cases, the gas output port 714 may be configured to engage a tube 732 inside the container 730 that brings received $CO_2$ to a space above liquid in the container 730, but this is not required.

The gas input port 712, the irrigation output port 720, and the lens wash port 724 may be configured to be quickly connected to the first tubing set 704 (e.g., $CO_2$ tubing or other suitable tubing), the second tubing set 706 (e.g., irrigation tubing or other suitable tubing) and the third tubing set 708 (e.g., lens wash tubing, such as a dual lumen tubing for carrying liquid and gas, or other suitable tubing), respectively. The gas input port 712, the irrigation output port 720, and the lens wash port 724 may be and/or may include spike ports, quick connect components, luer connection components, and/or other suitable fluid coupling mechanism configured to mate with the connectors of the respective tubing sets 704, 706, 708.

Figure 13:
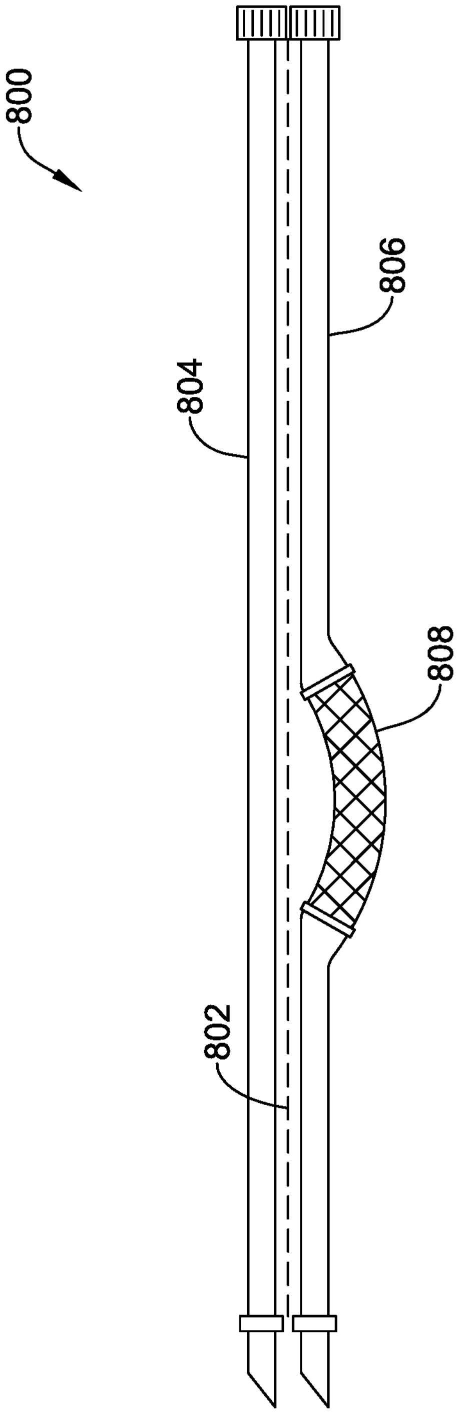
FIG. 13 depicts a schematic view of an illustrative dual extruded tubing set.
Figure 14:
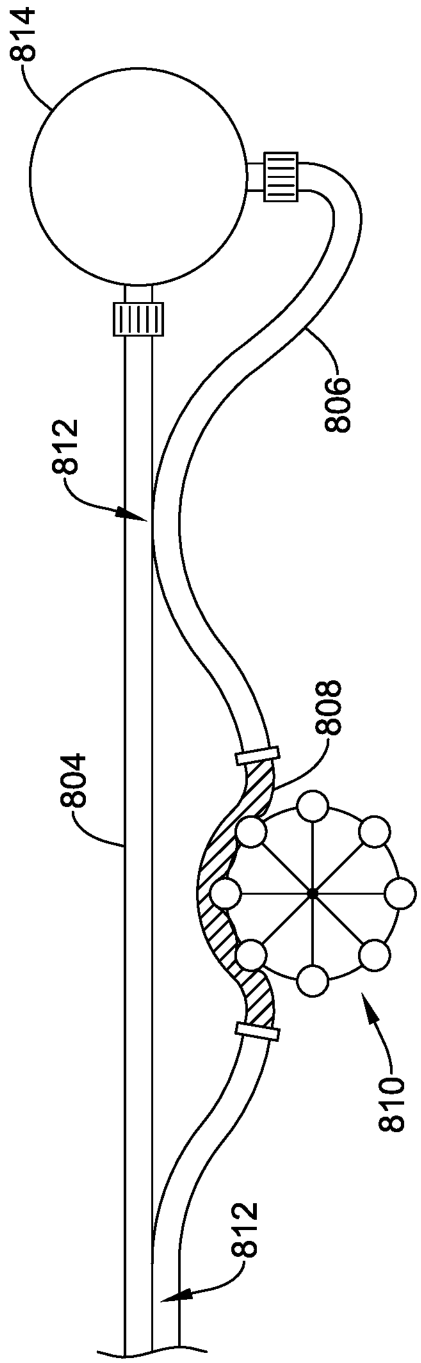
FIG. 14 depicts a schematic view of the illustrative dual extruded tubing set depicted in FIG. 13, with the dual extruded tubing set coupled to a pump an endoscopic controller.

FIGS. 13 and 14 depict schematic views of illustrative dual extruded tubes 800 with a tearable web or pre-cut notches 802 between a first tubing 804 and a second tubing 806 of the dual extruded tubes 800. In some cases, one or both of the first and second tubing 804, 806 may include a pump engaging portion 808 pre-formed to be separate or separated from the other one of the dual extruded tubing and configured to engage a peristaltic pump.

The tearable web or pre-cut notches 802 may have any suitable configuration configured to be extruded and to facilitate separating at least a portion of the first and second tubing 804, 806 from one another to facilitate connecting each of the first and second tubing 804, 806 to a desired tube connector on a manifold (e.g., the manifolds discussed herein or other suitable manifolds), the pump portion 808 to a pump, and/or other connectors while maintaining a connection of the first and second tubing 804, 806. Allowing the first tubing 804 to stay connected to the second tubing 806 may facilitate management of the tubing 804, 806 during use with an endoscope system.

The dual extruded tubes 800 may be formed from one or more suitable materials. Suitable materials include, but are not limited to, soft materials, flexible materials, polymers, metals, hard materials, silicone, PVC, and/or other suitable materials. In one example, one or both of the dual extruded tubes may be formed entirely or at least partially from a soft PVC. In another example, one or both of the dual extruded tubes may be formed entirely or at least partially from a silicone. Further. The first tubing 804 and the second tubing 806 may be formed from the same or different materials, as desired.

The first tubing 804 and the second tubing 806 of the dual extruded tubes 800 may have any suitable geometries. In one example configuration, one or both of the first tubing 804 and the second tubing 806 may have outer circumferences and/or lumens with inner circumferences of the tubing that have a circular cross-section. In another example configuration, one or both of the first tubing 804 and the second tubing 806 may have outer circumferences and/or lumens with inner circumferences of the tubing that have a D-shaped cross-section. When the first tubing 804 and the second tubing 806 both have D-shaped outer cross-sections, the flat or straight portion of the D-shaped outer cross-sections may be proximate or touching one another such that the first tubing 804 and second tubing 806 may be separated by pulling the flat or straight portions of the D-shape away from one another.

The first tubing 804 may be configured to be lens wash tubing and, in some cases, may be a dual lumen tube. A source of liquid (e.g., a bag, a bottle, etc.) to be passed through the first tubing 804 may be pressurized via pressurized air provided from the endoscope system and/or via pressurized $CO_2$ upon a call for lens wash fluid from an endoscope, as discussed herein or otherwise.

The second tubing 806 may be configured to be irrigation tubing and may include the pump portion 808 configured to engage a pump (e.g., a peristaltic pump) to pull liquid from the fluid source and provide high pressure liquid to the endoscope for irrigation purposes. FIG. 14 depicts the second tubing 806 separated from the first tubing to facilitate coupling the pump portion 808 to a peristaltic pump 810, while maintaining connection points 812 between the first tubing 804 and the second tubing 806. Similarly, the first tubing 804 and the second tubing 806 may be separated from one another to facilitate connecting ends of the first tubing 804 and the second tubing 806 to an endoscope umbilical and/or an endoscope controller 814, schematically depicted in FIG. 14.

The pump portion 808 of the second tubing 806 may have any suitable configuration. In some cases, the pump portion 808 may have a thinner wall than other portions of the second tubing to facilitate creating a flexible tube wall that can be manipulated by the pump 810 more easily than other portions of the second tubing 806.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A manifold for use with an endoscope system, the manifold comprising:

a fluid inlet;

a first fluid outlet;

a second fluid outlet;

a conduit in fluid communication with the fluid inlet and the first fluid outlet;

a pressurized chamber;

a compressible chamber in fluid communication with the conduit and in communication with the pressurized chamber;

an adjustable barrier between the compressible chamber and the pressurized chamber, wherein the adjustable barrier comprises a plunger configured to form a seal with a wall defining the compressible chamber and the pressurized chamber, and wherein a volume of the compressible chamber is configured to be reduced to cause fluid to pass through the second fluid outlet in response to a pressurized gas received at the pressurized chamber.

2. The manifold of claim 1, further comprising:

a one-way valve between the conduit and the compressible chamber, and wherein the one-way valve is configured to allow fluid to pass from the conduit into the compressible chamber and prevent fluid from passing to the conduit from the compressible chamber.

3. The manifold of claim 1, wherein the pressurized chamber is configured to receive pressurized air from an air pump.

4. The manifold of claim 1, wherein the pressurized chamber is configured to receive pressurized carbon dioxide ($CO_2$).

5. The manifold of claim 1, further comprising:

a gas port configured to receive the pressurized gas.

6. The manifold of claim 1, wherein the adjustable barrier adjusts to decrease the volume of the compressible chamber and increase a volume of the pressurized chamber in response to the pressurized chamber receiving the pressurized gas.

7. The manifold of claim 1, further comprising:

a spring in communication with the plunger, and wherein the spring is configured to bias the plunger to a first position associated with a first volume of the compressible chamber and the plunger is configured to adjust to a second position associated with a second volume of the compressible chamber in response to a pressure in the pressurized chamber acting on the plunger to overcome the bias of the spring.

8. The manifold of claim 1, wherein the adjustable barrier comprises a flexible material.

9. The manifold of claim 1, wherein the adjustable barrier is biased to a first position associated with a first volume of the compressible chamber and the flexible membrane is configured to adjust to a second position associated with a second volume of the compressible chamber in response to a pressure in the pressurized chamber acting on the adjustable barrier to overcome the bias.

10. The manifold of claim 1, further comprising:

a gas port in communication with the pressurized chamber and configured to receive the pressurized gas, and wherein the gas port and the second fluid outlet are configured to couple with a coaxial dual lumen tubing set.

11. The manifold of claim 1, further comprising:

a fluid access port in fluid communication with the conduit between the fluid inlet and the first fluid outlet.

12. A fluid supply system for an endoscope system, the fluid supply system comprising:

a container configured to contain fluid;

a manifold comprising:

a pressurized gas pathway;

a first fluid pathway configured to receive fluid from the container;

a second fluid pathway configured to receive fluid from the container;

a first port in fluid communication with the pressurized gas pathway;

a second port in fluid communication with the first fluid pathway;

a third port in fluid communication with the second fluid pathway;

a first bag spike configured to engage the container and in fluid communication with the pressurized gas pathway to provide pressurized gas to the container; and a second bag spike configured to engage the container and in fluid communication with the first fluid pathway and the second fluid pathway;

a first tubing set having a first end configured to couple to the second port and to be in communication with a pump; and a second tubing set having a first end configured to couple to the third port and to be in fluid communication with an endoscope of the endoscope system.

13. The fluid supply system of claim 12, wherein the first tubing set is releasably coupled to the second tubing set.

14. The fluid supply system of claim 12, wherein the first tubing set includes a pump engaging portion at a location between the first end and a second end of the first tubing set.

15. The fluid supply system of claim 12, wherein the manifold comprises a recess configured to receive the container and the first bag spike and the second bag spike extend from a surface of the recess.

16. The fluid supply system of claim 12, wherein the container comprises:

a pressurized chamber configured to receive pressurized fluid via the pressurized gas pathway and cause fluid to be output from the third port.

17. A manifold for use with an endoscope system, the manifold comprising:

an irrigation conduit configured to be in fluid communication with a source of fluid;

a lens wash chamber configured to receive liquid from the irrigation conduit via an inlet and output the liquid received from an outlet;

a pressurized chamber configured to receive pressurized gas; and an adjustable barrier between the pressurized chamber and the lens wash chamber, wherein the adjustable barrier comprises a plunger configured to form a seal with a wall defining the pressurized chamber and the lens wash chamber, and wherein the adjustable barrier is configured to adjust to push liquid through the outlet in response to the pressurized chamber receiving the pressurized gas.

* * * * *